(12) United States Patent
Greenwald et al.

(10) Patent No.: US 8,548,768 B2
(45) Date of Patent: *Oct. 1, 2013

(54) SYSTEM AND METHOD FOR EVALUATING AND PROVIDING TREATMENT TO SPORTS PARTICIPANTS

(75) Inventors: Richard M. Greenwald, Norwich, VT (US); Jeffrey J. Chu, Quechee, VT (US); David W. Bertoni, Beverly, MA (US); Thad M. Ide, Chicago, IL (US)

(73) Assignee: Riddell, Inc., Rosemont, IL (US)

(*) Notice: Subject to any disclaimer, the term of this patent is extended or adjusted under 35 U.S.C. 154(b) by 1056 days.

This patent is subject to a terminal disclaimer.

(21) Appl. No.: 11/328,445

(22) Filed: Jan. 9, 2006

(65) Prior Publication Data

US 2006/0189852 A1 Aug. 24, 2006

Related U.S. Application Data

(63) Continuation-in-part of application No. 11/225,880, filed on Sep. 13, 2005, and a continuation-in-part of application No. 10/997,832, filed on Nov. 24, 2004, and a continuation of application No. 09/974,566, filed on Oct. 10, 2001, now Pat. No. 6,826,509.

(60) Provisional application No. 60/642,240, filed on Jan. 7, 2005, provisional application No. 60/609,555, filed on Sep. 13, 2004, provisional application No. 60/239,379, filed on Oct. 11, 2000.

(51) Int. Cl.
- *G01P 15/00* (2006.01)
- *A61B 5/103* (2006.01)
- *G08B 23/00* (2006.01)

(52) U.S. Cl.
USPC .............. 702/141; 600/595; 340/573.1

(58) Field of Classification Search
USPC ........... 702/141, 57, 79, 127, 130, 131, 133, 702/138, 139, 182, 183, 189, 193; 600/300, 600/549, 587, 595, 301; 340/539.11, 539.12, 340/3.1, 3.3, 3.31, 3.32, 539.1, 539.16, 539.17, 340/57, 825.36; 128/903, 920
See application file for complete search history.

(56) References Cited

U.S. PATENT DOCUMENTS 3,646,606 A * 2/1972 Buxton et al. ............... 600/483
3,972,320 A   8/1976 Kalman (Continued)

FOREIGN PATENT DOCUMENTS

DE 19707495 A1 8/1998
WO 9904685 A 2/1999

(Continued)

OTHER PUBLICATIONS

Murray, C., smart Helmets Monitor Football Injuries, Dec. 18, 2003, Embedded.com.*

(Continued)

*Primary Examiner* — Toan Le
(74) *Attorney, Agent, or Firm* — McDermott Will & Emery LLP

(57) ABSTRACT

The invention relates to a system for monitoring a physiological parameter of players engaged in a sports activity and a method for evaluating and treating players when the parameter exceeds a predetermined level. The system measures, calculates and records the parameter and then alerts trained personnel to apply the method to evaluate and treat players. When the system is configured for use with football, hockey or lacrosse, the system generally includes reporting units, a sideline controller, a database, and a signaling device, such as a wireless personal digital assistant. The physiological parameter data measured and collected by the reporting units are processed by the sideline controller for meaningful analysis or use. When the physiological parameter(s) exceeds a predetermined threshold level the sideline controller generates an alert that is received by the signaling device, which is typically worn by sideline personnel, such as coaching staff or trainers. After an alert occurs, the method for evaluating and treating a player is initiated.

48 Claims, 11 Drawing Sheets

(56) References Cited

U.S. PATENT DOCUMENTS

| | | | |
|---|---|---|---|
| 4,440,160 A | | 4/1984 | Fischell et al. |
| 4,763,275 A | | 8/1988 | Carlin |
| 5,221,088 A | | 6/1993 | McTeigue et al. |
| 5,408,879 A | | 4/1995 | Vreeburg et al. |
| 5,539,935 A | * | 7/1996 | Rush, III .......................... 2/422 |
| 5,621,922 A | | 4/1997 | Rush, III |
| 5,916,181 A | | 6/1999 | Socci et al. |
| 5,978,972 A | * | 11/1999 | Stewart et al. .................... 2/422 |
| 6,002,994 A | * | 12/1999 | Lane et al. ...................... 702/188 |
| 6,057,758 A | * | 5/2000 | Dempsey et al. ........ 340/539.12 |
| 6,186,145 B1 | * | 2/2001 | Brown .......................... 128/897 |
| 6,198,394 B1 | * | 3/2001 | Jacobsen et al. ........... 340/573.1 |
| 6,259,944 B1 | | 7/2001 | Margulis et al. |
| 6,302,844 B1 | * | 10/2001 | Walker et al. ................. 600/300 |
| 6,366,871 B1 | * | 4/2002 | Geva ........................... 702/188 |
| 6,375,612 B1 | | 4/2002 | Guichon et al. |
| 6,441,747 B1 | * | 8/2002 | Khair et al. ............. 340/870.16 |
| 6,611,782 B1 | | 8/2003 | Wooster et al. |
| 6,611,789 B1 | * | 8/2003 | Darley ......................... 702/160 |
| 6,735,551 B2 | * | 5/2004 | Voegeli et al. ................ 702/183 |
| 6,748,250 B1 | * | 6/2004 | Berman et al. ................ 600/310 |
| 7,054,784 B2 | | 5/2006 | Flentov et al. |
| 7,386,401 B2 | | 6/2008 | Vock et al. |
| 7,526,389 B2 | | 4/2009 | Greenwald et al. |
| 7,693,668 B2 | | 4/2010 | Vock et al. |
| 2002/0024450 A1 | * | 2/2002 | Townsend et al. ....... 340/870.16 |
| 2002/0060633 A1 | | 5/2002 | Crisco et al. |
| 2006/0074338 A1 | * | 4/2006 | Greenwald et al. ........... 600/549 |

FOREIGN PATENT DOCUMENTS

| | | |
|---|---|---|
| WO | 02053024 A | 7/2002 |
| WO | 2006036567 A | 4/2006 |

OTHER PUBLICATIONS

Puers et al., A Telemetry System for the Detection of Hip Prosthesis Loosening by Vibration Analysis, Aug. 25, 2000, Sensors and Actuators, vol. 85, pp. 42-47.*

Bai et al., A Portable ECG and Blood Pressure Telemonitoring System, Jul./Aug. 1999, IEEE Engineering in Medicine and Biology, pp. 63-70.*

Moon et al., Peak Head Acceleration of Athletes during Competition—Football, Spring 1971, Medicine and Science in Sports, vol. 3, No. 1, pp. 44-50.*

Merono et al., Movement Evaluator System Via R.F. Transmission, 1995 IEEE, pp. 94-97.*

Coleman et al., Ambient Head Temperature and Football Helmet Design, Mar. 1972, Medicine, Science, Exercise and Sports Journal, 19 pp.*

International Search Report for PCT/US2006/000536 mailed Oct. 2, 2006.

* cited by examiner

SYSTEM AND METHOD FOR EVALUATING AND PROVIDING TREATMENT TO SPORTS PARTICIPANTS

CROSS-REFERENCE TO RELATED APPLICATIONS

This application claims priority from U.S. Provisional Patent Application No. 60/642,240, filed Jan. 7, 2005, and is a continuation-in-part (CIP) application of U.S. application Ser. No. 11/225,880, filed Sep. 13, 2005, which claimed priority from U.S. Provisional Patent Application No. 60/609,555, filed Sep. 13, 2004, and is a continuation-in-part (CIP) application of U.S. patent application Ser. No. 10/997,832, filed Nov. 24, 2004 and is a continuation of U.S. application Ser. No. 09/974,566, filed Oct. 10, 2001, now U.S. Pat. No. 6,826,509, which claimed priority from U.S. Provisional Patent Application No. 60/239,379, filed Oct. 11, 2000.

FEDERALLY SPONSORED RESEARCH OR DEVELOPMENT

A portion of the invention described herein was made in the course of work under grant number 1R43HD4074301 from the National Institute of Health. The U.S. Government may retain certain rights in this invention.

TECHNICAL FIELD

The invention relates to a system for monitoring physiological parameters of players engaged in a sports activity. The invention further relates to a method for evaluating and treating players when the parameter exceeds a predetermined level. The system measures, calculates and records the parameters and then alerts trained personnel to apply the method to evaluate and treat players.

BACKGROUND OF THE INVENTION

There is a concern in various contact sports, such as football and hockey, of brain injury due to impact to the head. During such physical activity, the head or other body part of the individual is often subjected to direct contact to the head which results in impact to the skull and brain of the individual as well as movement of the head or body part itself.

Much remains unknown about the response of the brain to head accelerations in the linear and rotational directions and even less about the correspondence between specific impact forces and injury, particularly with respect to injuries caused by repeated exposure to impact forces of a lower level than those that result in a catastrophic injury or fatality. Almost all of what is known is derived from animal studies, studies of cadavers under specific directional and predictable forces (i.e. a head-on collision test), from crash dummies, from human volunteers in well-defined but limited impact exposures or from other simplistic mechanical models. The conventional application of known forces and/or measurement of forces applied to animals, cadavers, crash dummies, and human volunteers limit our knowledge of a relationship between forces applied to a living human head and resultant severe and catastrophic brain injury. These prior studies have limited value as they typically relate to research in the automobile safety area.

The concern for sports-related injuries, particularly to the head, is higher than ever. The Center for Disease Control and Prevention estimates that the incidence of sports-related mild traumatic brain injury (MTBI) approaches 300,000 annually in the United States. Approximately ⅓ of these injuries occur in football. MTBI is a major source of lost player time. Head injuries accounted for 13.3% of all football injuries to boys and 4.4% of all soccer injuries to both boys and girls in a large study of high school sports injuries. Approximately 62,800 MTBI cases occur annually among high school varsity athletes, with football accounting for about 63% of cases. Concussions in hockey affect 10% of the athletes and make up 12%-14% of all injuries.

For example, a typical range of 4-6 concussions per year in a football team of 90 players (7%), and 6 per year from a hockey team with 28 players (21%) is not uncommon. In rugby, concussion can affect as many as 40% of players on a team each year. Concussions, particularly when repeated multiple times, significantly threaten the long-term health of the athlete. The health care costs associated with MTBI in sports are estimated to be in the hundreds of millions annually. The National Center for Injury Prevention and Control considers sports-related traumatic brain injury (mild and severe) an important public health problem because of the high incidence of these injuries, the relative youth of those being injured with possible long term disability, and the danger of cumulative effects from repeat incidences.

Athletes who suffer head impacts during a practice or game situation often find it difficult to assess the severity of the blow. Physicians, trainers, and coaches utilize standard neurological examinations and cognitive questioning to determine the relative severity of the impact and its effect on the athlete. Return to play decisions can be strongly influenced by parents and coaches who want a star player back on the field. Subsequent impacts following an initial concussion (MTBI) may be 4-6 times more likely to result in a second, often more severe, brain injury. Significant advances in the diagnosis, categorization, and post-injury management of concussions have led to the development of the Standardized Assessment of Concussion (SAC), which includes guidelines for on-field assessment and return to sport criteria. Yet there are no objective biomechanical measures directly related to the impact used for diagnostic purposes. Critical clinical decisions are often made on the field immediately following the impact event, including whether an athlete can continue playing. Data from the actual event would provide additional objective data to augment psychometric measures currently used by the on-site medical practitioner.

Brain injury following impact occurs at the tissue and cellular level, and is both complex and not fully understood. Increased brain tissue strain, pressure waves, and pressure gradients within the skull have been linked with specific brain injury mechanisms. Linear and rotational head acceleration are input conditions during an impact. Both direct and inertial (i.e. whiplash) loading of the head result in linear and rotational head acceleration. Head acceleration induces strain patterns in brain tissue, which may cause injury. There is significant controversy regarding what biomechanical information is required to predict the likelihood and severity of MTBI. Direct measurement of brain dynamics during impact is extremely difficult in humans.

Head acceleration, on the other hand, can be more readily measured; its relationship to severe brain injury has been postulated and tested for more than 50 years. Both linear and rotational acceleration of the head play an important role in producing diffuse injuries to the brain. The relative contributions of these accelerations to specific injury mechanisms have not been conclusively established. The numerous mechanisms theorized to result in brain injury have been evaluated in cadaveric and animal models, surrogate models, and computer models. Prospective clinical studies combining head impact biomechanics and clinical outcomes have been strongly urged. Validation of the various hypotheses and models linking tissue and cellular level parameters with MTBI in sports requires field data that directly correlates specific kinematic inputs with post-impact trauma in humans.

In the prior art, conventional devices have employed testing approaches which do not relate to devices which can be worn by living human beings, such as the use of dummies. When studying impact with dummies, they are typically secured to sleds with a known acceleration and impact velocity. The dummy head then impacts with a target, and the accelerations experienced by the head are recorded. Impact studies using cadavers are performed for determining the impact forces and pressures which cause skull fractures and catastrophic brain injury.

There is a critical lack of information about what motions and impact forces lead to MTBI in sports. Previous research on football helmet impacts in actual game situations yielded helmet impact magnitudes as high as 530 g's for a duration of 60 msec and >1000 g's for unknown durations with no known MTBI. Accelerometers were held firmly to the head via the suspension mechanism in the helmet and with Velcro straps. A recent study found maximum helmet accelerations of 120 g's and 150 g's in a football player and hockey player, respectively. The disparity in maximum values among these limited data sets demonstrates the need for additional large-scale data collection.

Most prior art attempts relate to testing in a lab environment. However, the playing field is a more appropriate testing environment for accumulating data regarding impact to the head. A limitation of the prior art involves practical application and widespread use of measurement technologies that are size and cost effective for individuals and teams. Therefore, there would be significant advantage to outfitting an entire playing team with a recording system for monitoring impact activities. This would assist in accumulating data of all impacts to the head, independent of severity level, to study the overall profile of head impacts for a given sport. Also, full-time head acceleration monitoring would also be of great assistance in understanding a particular impact or sequence of impacts to a player's head over time that may have caused an injury and to better treat that injury medically.

Conventional devices do not include a system which immediately measures, calculates and records the magnitude and direction of an impact to the player's body part. In addition, conventional devices do not provide a method or protocol for qualified sideline personnel to evaluate and treat a player who sustains an impact to the body part. Further, no conventional devices are integrated such that a system prompts the method for evaluating and treating a player who sustains such an impact. Conventional devices also lack a wireless device that can be utilized on an interactive basis to evaluate and treat a player who sustains such an impact.

The present invention is provided to solve the problems discussed above and other problems, and to provide advantages and aspects not provided by prior systems of this type. A full discussion of the features and advantages of the present invention is deferred to the following detailed description, which proceeds with reference to the accompanying drawings.

SUMMARY OF THE INVENTION

The present invention provides a system for monitoring physiological parameters of players engaged in a sports activity. The invention further relates to a method for evaluating and treating players when the parameter exceeds a predetermined level. The system measures, calculates and records the parameters, and then alerts trained personnel to apply the method to evaluate and treat players. The system and method are especially well suited for helmeted team sports where players are susceptible to head impacts and injuries; for example, football, hockey, and lacrosse.

According to one aspect of the invention, the system includes multiple reporting units, a controller unit, a signaling device, a database, and software that enables the various components of the system to communicate and interact. The reporting unit is configured for use with a variety of protective gear, such as a helmet, head band, leg guard, or shoulder pad. Because most teams include numerous players, in some cases exceeding one hundred players, each player has a recording unit that communicates with the controller. Therefore, the recording units continuously and collectively measure and transmit physiological data to the controller for monitoring of the players. While a significant portion of the parameter measurement and monitoring occurs during the course of play, the system continues to measure relevant physiological parameters, such as the players' body temperature, when players are at a reduced activity level on the sideline. The system may be configured without the controller, whereby the reporting units interact and communicate directly with the signaling device.

According to another aspect of the invention, the system is integrated with a method for evaluating and treating a player. The method includes a number of steps to be performed by qualified sideline personnel, such as trainers, coaches, and/or medical staff, which typically are on or near the sidelines of a sporting event or practice. The method utilizes a software package or interactive wizards that are loaded onto the signaling device, such as a personal digital assistant (PDA). When a physiological parameter exceeds a predetermined limit resulting in an alert event, the controller sends a signal to the signaling device providing relevant information about the alert event. For each alert event, the signaling device displays the affected player's number and medical history, the time of the event, and the physiological parameter to be evaluated. The interactive wizards provide testing baselines and an interactive protocol for guiding sideline personnel through appropriate examination procedures. The signaling device records the results and transmits the results to the controller and/or the database for use in further evaluation and treatment of the player. Therefore, whenever an alert event occurs and a potentially injured player is brought to the sideline for evaluation, the signaling device displays the individual's medical and injury history, the results of previous evaluations and other pertinent medical data. Then, the signaling device, through the interactive wizards, prompts the sideline personnel to conduct the appropriate sideline examination, records the responses, compares the results to established baselines, and may prompt further testing. The sideline personnel, which may include certified trainers and/or medical staff, such as physicians, utilize the stored results to evaluate the severity of the player's condition and to make a return to play (RTP) decision or a no return to play decision for the player.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying exhibits in which.

DETAILED DESCRIPTION

Figure 1:
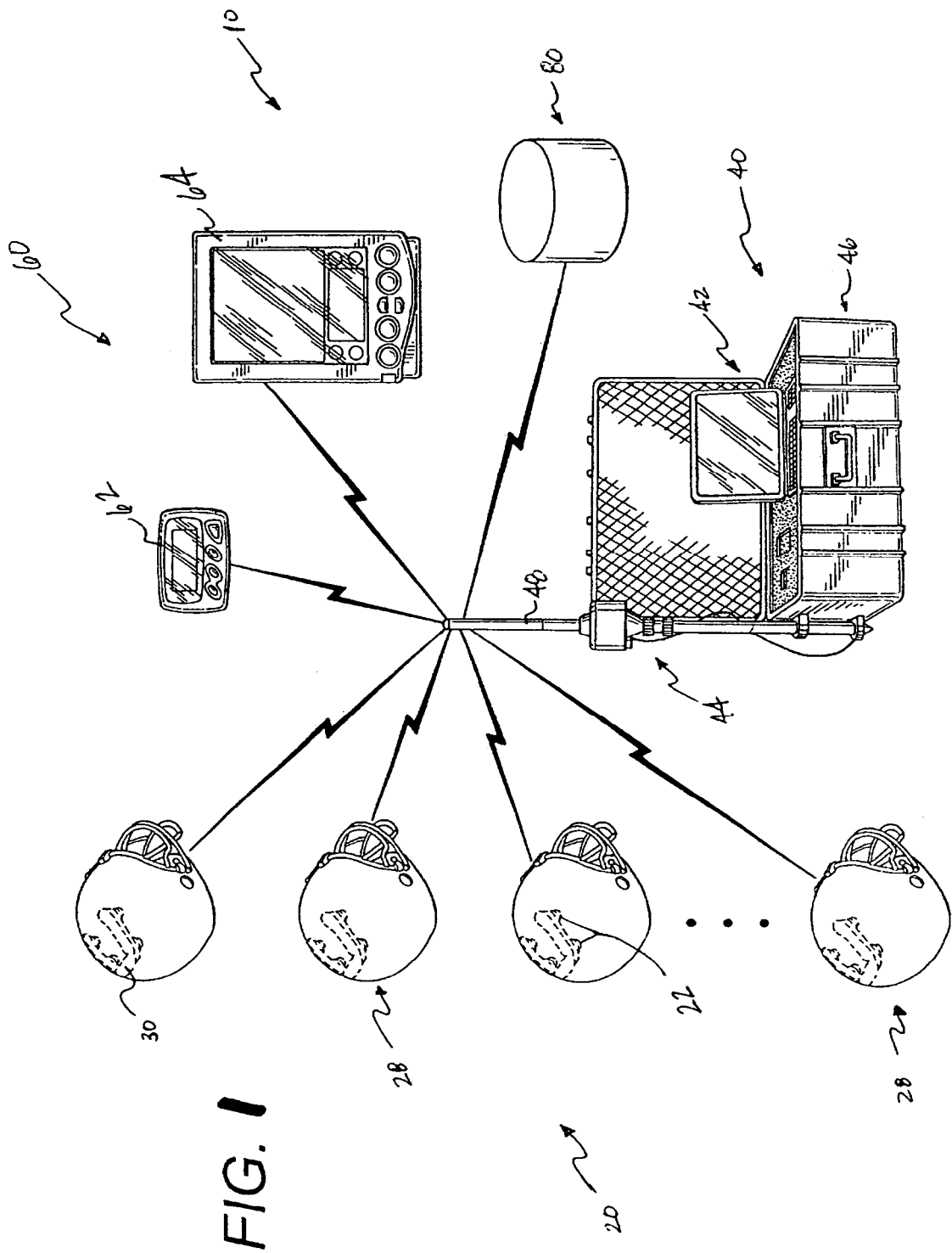
FIG. 1 is a perspective view of a system and method of the present invention.

While this invention is susceptible of embodiments in many different forms, there are shown in the drawings and will herein be described in detail preferred embodiments of the invention with the understanding that the present disclosure is to be considered as an exemplification of the principles of the invention and is not intended to limit the broad aspect of the invention to the embodiments illustrated.

FIGS. 1-10 depict a multi-component system 10 for actively monitoring physiological parameters of numerous players engaged in a sporting activity, wherein the system 10 interacts with the method for evaluating and treating players based upon the results of the monitored parameter. In one embodiment, the players' parameter data is transmitted, via a wired or wireless connection, to a controller for calculation and then to a signaling device for use by trained personnel to employ the method for player evaluation and treatment. The system 10 may be configured to measure and calculate the acceleration of a body part (e.g., the head) of players while engaged in physical activity, such as during play of a contact sport. In another embodiment, the system 10 is designed to measure and calculate each player's body temperature during play. In yet another embodiment, the system 10 is designed to measure and calculate both the acceleration of each player's body part and the player's temperature during play. When a calculated parameter result approaches or exceeds a predetermined level, the qualified sideline personnel utilize the method of the present invention to evaluate and treat the player(s) in question. Since most contact sports involve multi-player teams, the system 10 simultaneously measures, records and transmits the data on the physiological parameters for all players on the team throughout the course of play, including a game or practice. The system 10 is especially well suited for helmeted team sports where players are susceptible to head impacts and injuries; for example, football, hockey, and lacrosse. The system 10 could also be employed in sports where helmets are not traditionally worn; for example, rugby or soccer.

The system 10 is generally comprised of multiple reporting units 20, a controller unit 40, a signaling device 60, a database 80, and software 90 that enables the various components of the system 10 to communicate and interact. While the system 10 is described below in the context of a helmeted team sport, the system 10 can be utilized in connection with other sporting activities that do not require a helmet, such as soccer or rugby. Consequently, the system 10 can be configured for use with other protective gear, such as a head band, leg guard, or shoulder pad. Because a football team includes numerous players, in some cases exceeding one hundred players, each player has a recording unit 20 that communicates with the controller 40. Therefore, the recording units 20 continuously and collectively measure and transmit physiological data to the controller for monitoring of the players. While a significant portion of the parameter measurement and monitoring occurs during the course of play, the system 10 continues to measure relevant physiological parameters, such as the players' body temperature, when players are at a reduced activity level on the sideline.

The reporting unit 20 automatically and continuously measures and records the player's physiological parameters and transmits data regarding the parameter to the controller 40. When the system 10 is configured for use with a football team, the wearable reporting unit 20 is adapted for use either within each player's helmet or protective gear, such as shoulder pads. Referring to FIGS. 1-4 and as explained in co-pending U.S. patent application Ser. No. 11/225,880 which is incorporated herein by reference, the reporting unit 20 includes a sensor assembly defined by a plurality of sensors 22 that measures the player's physiological parameter and a control unit 24, wherein the sensors 22 are operably connected to the control unit 24. As shown in FIG. 3, a wire lead 26 electrically connects each sensor 22 with the control unit 24. The control unit 24 can include a signal conditioner 24a, a filter 24b, a microcontroller 24c (or microprocessor), a telemetry element 24d, an encoder 24e, and a power source 24f. While the encoder 24e is shown as separate from the telemetry element 24d, the encoder 24e can be integrated within the telemetry element 24d. The sensors 22 are calibrated to measure the player's physiological condition or parameter and then generate input data regarding each parameter. The control unit 24 processes the input data, including filtering and conditioning as necessary, and then converts the data to signals. Next, the encoder 24e of the control unit 24 encodes the signals with a unique identifier, and the telemetry element 24d wirelessly transmits (as represented by the lightning bolts in FIG. 1) the encoded signals to the remote controller 40 which recognizes the encoded signals for further processing and calculation. The telemetry element 24d can be a transceiver, or a separate receiver and transmitter. The power source 24f can be a rechargeable battery or a disposable battery. In another embodiment of the system 10, the parameter data transmitted from the reporters 20 to the controller 40 can be encrypted to increase the security of the underlying data. In this configuration, the system 10 can include a cipher for performing encryption and decryption, and a key to parameterize the cipher. The reporting unit 20 can transmit parameter data during the course of play or between plays via a wireless transmitter to the controller 40. Alternatively, the reporting unit 20 transmits parameter data during prolonged stoppages of play, such as intermission or half-time, or after the completion of play or the game via a wired connection to the controller 40. In the wired configuration, the reporting unit 20 transfers parameter data with a wired protocol, such as I2C, SPI, USB, RS 232 or others. Due to the wired connection between the reporting unit 20 and the controller 40, the reporting unit 20 need not include the telemetry element 24d and/or the encoder 24e.

The type of sensors 22 within the reporting unit 20 depends upon the player's physiological data to be measured, transmitted and monitored. For example, when the reporting unit 20 is configured to measure acceleration of the body part, the sensors 22 are single-axis accelerometers, multi-axis accelerometers, or a combination of both. As another example, to measure the player's temperature, each reporting unit 20 includes at least one sensor 22 such as a thermistor, which comprises resistive circuit components having a high negative temperature coefficient of resistance so that the resistance decreases as the temperature increases. Alternatively, the temperature sensor 22 is a thermal ribbon sensor or a bandgap type integrated circuit sensor. To measure both the acceleration and temperature of the player's body part, the sensors 22 can be a combination of accelerometers and thermistors operably connected to the control unit 24. Where the system 10 is configured for use with a football team to measure and monitor head acceleration and player body temperature, the sensors 22 are accelerometers and thermistors that are arrayed in an in-helmet unit 28 (see FIG. 4) for each player. To measure other physiological parameters, such as the player's heart rate and blood pressure, the sensors 22 are micro electro-mechanical system (MEMS) type sensors that use auscultatory and/or oscillometric measurement techniques. In another embodiment, the sensors 22 may include low acceleration (low G) accelerometers that are configured to measure small movements of the player's head consistent with balance problems. The system 10 includes an algorithm that calculates and observes a player's balance between plays or during extended stoppages in play, such as when a penalty is being assessed or a timeout. In this manner, the player's physiological parameter can be measured on the field of play, instead of the sideline. When a player assumes the ready position prior to the commencement of the play, for example a three-point stance, the low G accelerometers and the algorithm would detect player movements indicative of balance problems and a concussion.

Figure 3:
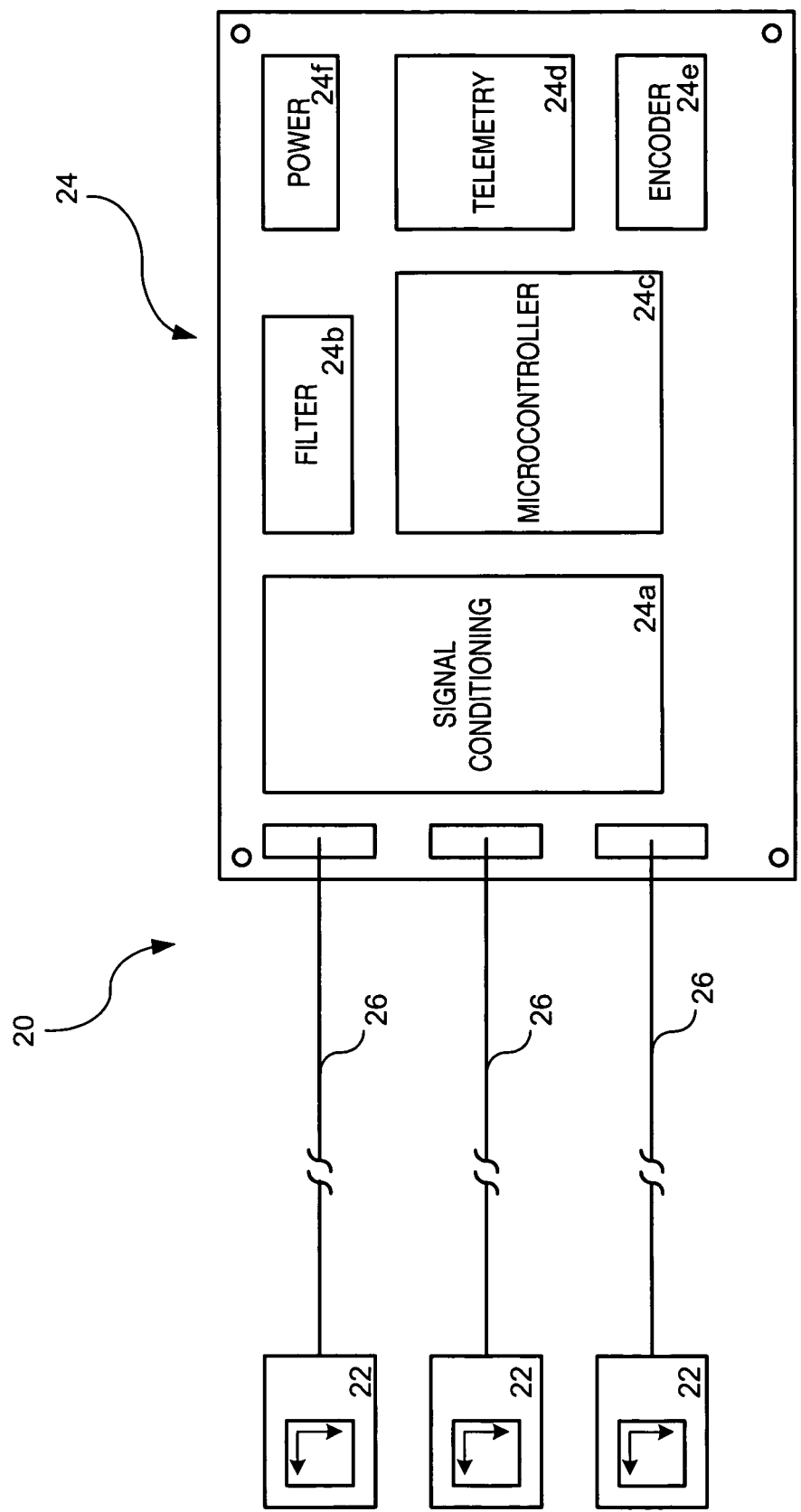
FIG. 3 is a schematic of a reporting unit of the system of the invention.
Figure 4:
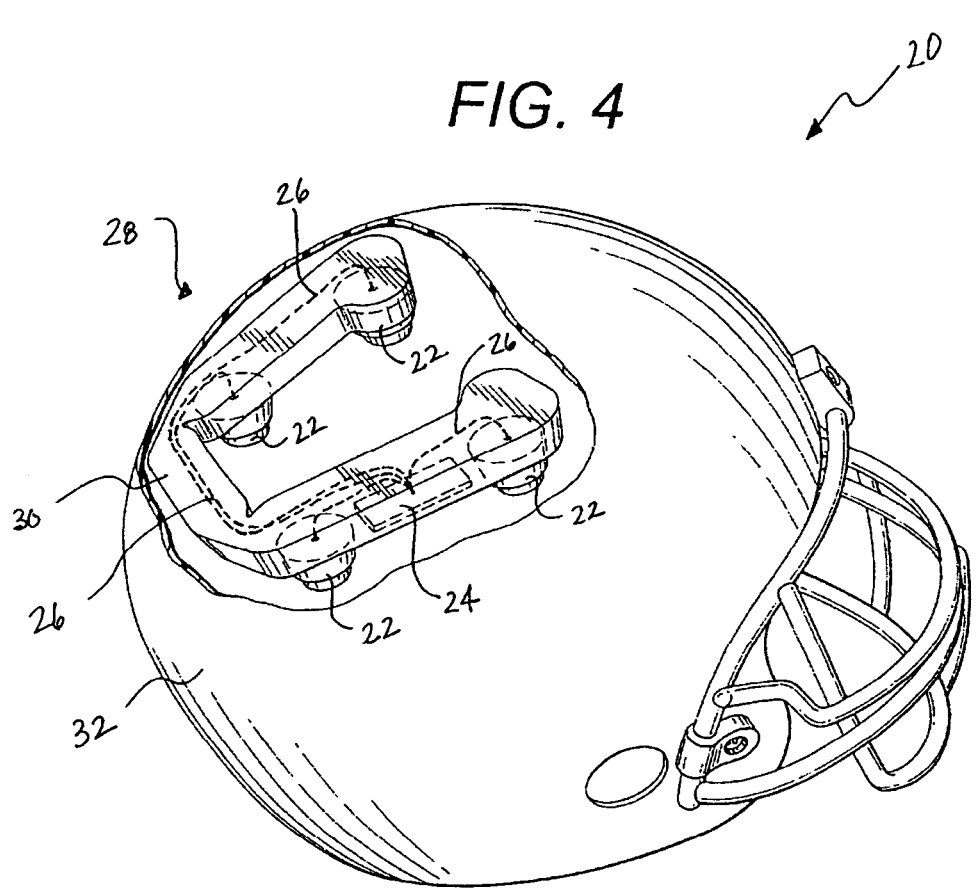
FIG. 4 is a perspective view of the reporting unit of the system installed in a helmet.
Figure 5:
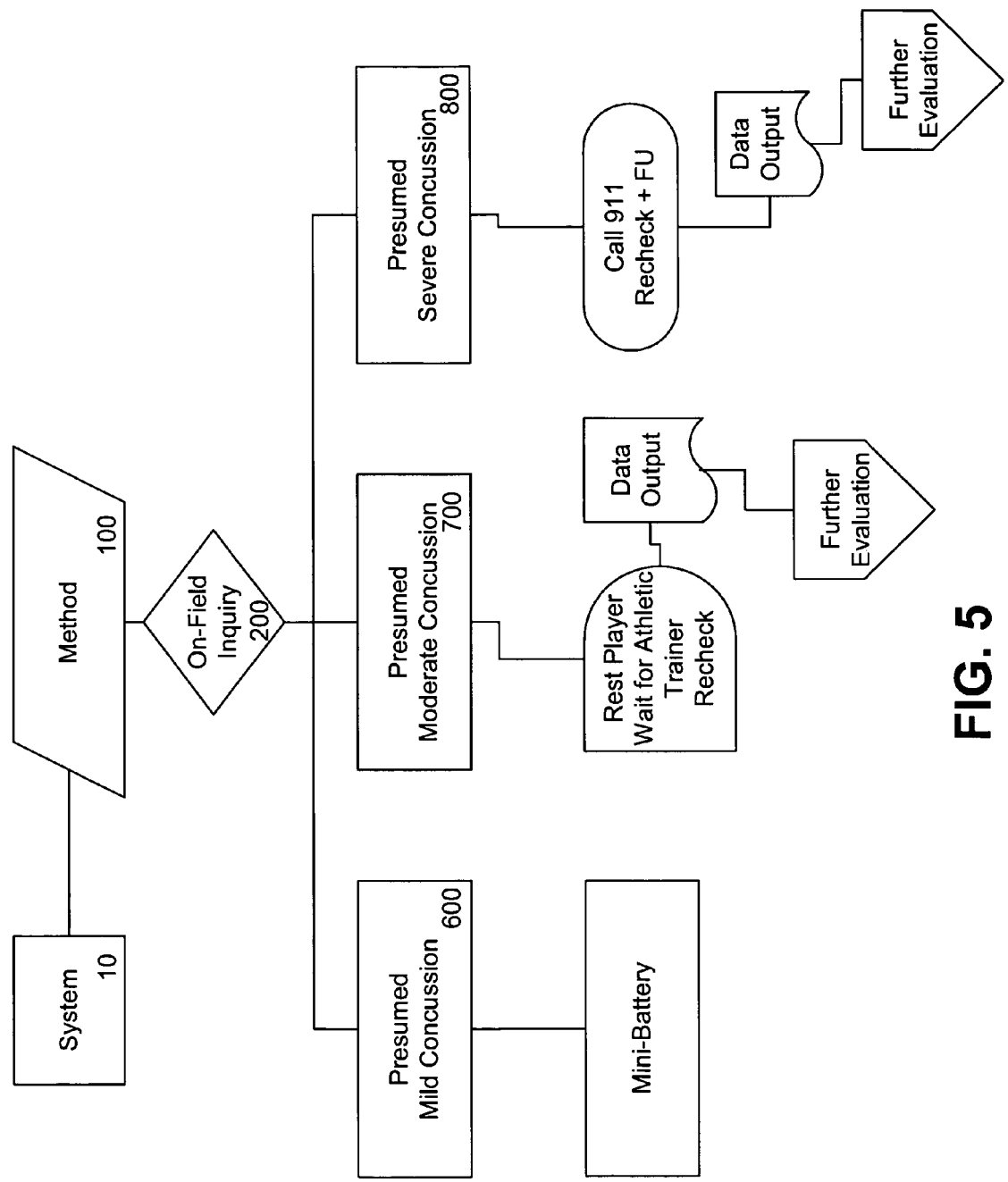
FIG. 5 is a flowchart of the system and method, showing three grades of concussions to be monitored and treated.

As shown in FIG. 4, the in-helmet unit 28 includes a flexible band 30 that houses the sensors 22 and the control unit 24. The flexible band 30 is received within the internal padding assembly of the helmet 32, wherein the sensors 22 are positioned about the player's skull. In this manner, the in-helmet unit 28 is removably received within the helmet 32 to allow for testing and maintenance, including recharging of the battery power source. In one embodiment where the system 10 measures the acceleration of the player's head, the band 30 is dimensioned such that the sensitive axis of each accelerometer sensor 22 is orthogonal to the outer surface of the player's head. In another embodiment, the accelerometer sensors 22 are not positioned orthogonal to the head surface. Depending upon the other design parameters of the system 10, the accelerometer sensors 22 can be positioned either orthogonally or non-orthogonally to each other. While FIG. 3 depicts three sensors 22 within the reporting unit 20, the precise number of sensors 22 varies with the design of the system 10. In the embodiment where the system 10 measures the player's temperature, the temperature sensor 22 can be placed within the forehead pad of the helmet 32 or at other locations in protective equipment, such as shoulder pads, knee pads, etc.

In operation, the reporting unit sensors 22 measure the physiological parameter(s) and generate signals in response to the measured parameter value. The sensors 22 can be configured to continuously generate signals in response to the parameter value, or generate signals only when the parameter value reaches or exceeds a threshold level. For example, the sensors 22 can be single-axis accelerometers that measure head acceleration but only generate signals when the sensed head acceleration surpasses 10 G's. The control unit 24 processes the data signals and transmits them to the sideline controller 40 for calculation and monitoring of the player's physiological condition. As part of the processing step, the control unit 24 conditions and filters the signals, as necessary, and then encodes the signals with a unique player identifier for transmission to the controller 40. To support simultaneous transmissions from multiple reporters 20 to the correct controller 40, the signals sent from each control unit 24 can be divided with time division multiple access (TDMA), code division multiple access (CDMA), or frequency division multiple access (FDMA) technology. Encoding the signals with a unique identifier enables the controller 40 to properly multiplex and decode information from the various reporters 20 transmitting data. Accordingly, the system 10 simultaneously measures and transmits encoded data from a number of reporters 20, and then the controller 40 catalogs either the encoded data signal for further calculation, or the resultant calculation based upon the relationship between the reporter 20 and the player. Regardless of when the cataloging occurs, the controller 40 organizes each player's calculated parameter result for further analysis and/or monitoring. In one embodiment, an operator of the system 10 defines the relationship or association between the reporter 20 and the player when the player is issued a helmet or protective gear having the reporter 20. With the aid of the signaling device 60, the sideline personnel utilizing the system 10 can then monitor the physiological condition of select players based upon the cataloging of the calculated parameter result.

Generally, the controller 40 receives the data measured and transmitted by the reporting units 20 and processes the data for meaningful analysis or use. The sideline controller 40 is comprised of a portable microprocessor 42 (e.g., a laptop or portable computer), including a display screen, and a telemetry element 44 operably connected to the microprocessor 42. The controller 40 is a mobile apparatus that can be transported in a case 46. Referring to FIG. 2, the telemetry element 44 includes an antenna 48, a transmitter 50, a receiver 52 (or a combined transceiver), and an encoder 54. Consistent with that explained above, the telemetry element 44 decodes the encoded signals sent from each reporter 20, and the controller 40, primarily the microprocessor 42, performs the requisite calculation and then multiplexes the results according to the player identifier provided by the reporting unit 20. In this manner, the controller 40 recognizes the identifier provided by each reporter 20 and organizes the results for each player having a reporter 20. Alternatively, the controller 40 catalogs the encoded signals, the telemetry element 44 decodes the signals allowing the microprocessor 42 to perform the requisite calculation, and then the controller 40 multiplexes the results according to the player identifier. The controller 40 has a local memory device for storing data received from the reporting units 20 and the subsequently calculated results. Preferably, the memory device of the controller 40 is capable of storing information compiled over an entire season, so if necessary, sideline personnel and/or medical staff can retrieve historical player data when needed. In preferred embodiments, the controller 40 is equipped with software 92 that includes team management information (e.g., complete roster list of players, position of players, identification of active players, etc.) and daily exposure information (e.g., date, game vs. practice, conditions, etc.). The controller 40 also is used to synchronize local data (e.g., one team or historical data) with the centralized database 80.

In operation, the controller 40 receives the encoded signal from the reporting unit 20 for the measured physiological parameter (the "Measured Parameter") and processes the data within the signal to calculate a result for the parameter (the "Parameter Result"). When the Parameter Result reaches or exceeds a predetermined parameter level (hereinafter the "Alert Event"), the controller 40 wirelessly communicates with the signaling device 60, via the transmitter 50, thereby alerting the sideline personnel bearing the device 60 of the Alert Event. For each Alert Event, the controller 40 displays the affected player's identity, for example by name or jersey number, the Measured Parameter, and the time of the Alert Event. However, the player's identity can be protected by use of a unique player identifier, which may be encoded or encrypted. When the Parameter Result falls below the level and an Alert Event does not occur, the controller 40 continues to receive data from the reporters 20 and performs the requisite calculations. Further, while an Alert Event arises from one reporter 20, the controller 40 continues to receive and process data from the other reporters 20. Thus, the system 10 provides active monitoring for all players having a reporter 20. The time stamp provided by the controller 40 allows sideline personnel and medical staff to correlate the calculated parameter to actual videotape of the sporting event that led to the Alert Event. Once an Alert Event has occurred, the controller 40 sends a signal to the signaling device 60 that alerts the sideline personnel to employ the method 100 for evaluating and treating the player in question, as explained below. The player in question is quickly identified by the controller 40 due to the unique identifier provided by the reporting units 20 and the subsequent recognition of the identifier and the multiplexing performed by the controller 40. In this manner, the sideline personnel can efficiently evaluate the player in question from among the many players comprising the team.

In an embodiment of the system 10 where the Measured Parameter is player head acceleration, when an Alert Event occurs, the controller 40 calculates the point of impact on the player's body part, the cumulative impacts sustained by the player during the current monitoring session, and then graphs the magnitude and duration of recent impacts to the player and/or the body part. As part of this calculation, the controller 40 uses an algorithm to estimate the magnitude of the impact measured by the sensors 22, wherein the algorithm comports with the disclosure of co-pending U.S. patent application Ser. No. 10/997,832. As an example, when the system 10 calculates a Parameter Result of 80 g's of head acceleration, which exceeds a predetermined threshold of 50 g's, an Alert Event results wherein the controller 40 sends a signal to the signaling device 60 providing information to sideline personnel to commence the method 100 for evaluating and treating the player that sustained the Alert Event.

In the embodiment where the system 10 monitors each player's body temperature, the controller 40 receives data from the reporting units 20 and then calculates each player's body surface temperature, the rate of temperature increase and/or decrease versus a selected time interval. In addition to the temperature sensor 22 in the reporting unit 20, the controller 40 can include an additional temperature and/or humidity sensor to measure ambient conditions and use the resulting data for correction purposes. When the system 10 is configured for player body temperature monitoring in helmeted team sports, the reporting unit 20 can be positioned within the helmet 32 or within other protective equipment worn by each player, such as a shoulder pad assembly. The controller 40 receives the temperature data from each reporter 20 and then applies an algorithm to calculate the player's body surface temperature, the rate of temperature increase and/or decrease, and other temperature-based parameters that aid in the evaluation of player thermal management.

As explained above, the signaling device 60 communicates with the controller 40 and provides notice of an Alert Event to the sideline personnel. Preferably, the signaling device 60 is a portable electronic device, such as a pager 62, a personal digital assistant (PDA) 64, a cellular telephone, or other electronic device that is capable of receiving data and displaying results transmitted by the controller 40. Typically, the device 60 is worn or held by sideline personnel, including the training staff, medical personnel and/or coaches. Depending upon the parameters of the system 10, the signaling device 60 could vibrate or sound an audio alarm when a suspect event is measured and recorded, and inform the wearer of the device 60 of the Alert Event. Regarding the nature of the Alert Event, the device 60 can advise of: the identity of player(s) affected; the nature of the suspect event, including an elevated head acceleration due to impact or a change in a player's physiological status such as elevated body temperature; and the time of the incident.

As part of the method 100 of evaluating and treating players that experience an Alert Event, the signaling device 60 is programmed with interactive software 95 that assures best practices are followed in the treatment and documentation of injuries, such as mild traumatic brain injuries (MTBI). The interactive software 95 may include a bundle of team management programs which enables the signaling device 60 to store all team data, including medical histories and testing baselines. The software 95 also provides the signaling device 60 with an active response protocol for guiding sideline personnel through appropriate examination procedures and recording the results. For example, when an Alert Event occurs and the relevant player is brought to the sideline for evaluation, the signaling device 60 can display the individual's head-injury history, the results of previous evaluations and other pertinent medical data. With the assistance of the software 95, the signaling device 60 prompts the medical staff member to conduct the appropriate sideline examination, records the responses, compares the results to established baselines and prompts either further testing or a play/no-play decision. The software 95 further includes a bundle of team management tools that includes a roster program which contains all the basic information about each individual player: e.g., contact information, which sports they play (including position and jersey number), emergency information, relevant sizes, equipment issues and availability to play. Information can be stored and sorted in a variety of ways, such as by team, person item and size. The software 95 may also include a session manager program that allows the coaching staff to document incidents as they occur during a practice or a game. The appropriate information about the team, players and conditions is entered at the beginning of each session. Then, as injuries occur, the software 95 provides a template for recording injury data on a per player basis. The data and results stored on the device 60 can be uploaded to the database 80 wherein authorized users can access same for team management and player evaluation functions.

In another embodiment of the inventive system 10 and method, the controller 40 is omitted and the reporting units 20 interact and communicate directly with the signaling device 60. In one version of this embodiment, the reporting units 20 measure the physiological parameters as explained above and perform the related calculations within their control unit 24. All of the calculated results are then transmitted from each reporting unit 20 to the signaling device 60, for example the PDA 64, for recordation and monitoring. The device 60 sorts and multiplexes the results while looking for an Alert Event. When the device 60 finds an Alert Event, the device 60 alerts the sideline personnel consistent with that explained above.

Alternatively, each reporting unit 20 performs the necessary calculations to arrive at a Parameter Result and then transmits only those results that amount to an Alert Event. In this manner, the reporting unit 20 calculates and transmits the Alert Event whereby the device 60 receives signals from a reduced number of reporters 20—only those transmitting an Alert Event. In another version of this embodiment, the reporting units 20 measure the physiological parameters and transmit the data signals to the device 60, for example the PDA 64, wherein the device 60 performs the related calculations to arrive at the Parameter Result. When the Parameter Result amounts to an Alert Event, the device 60 alerts the sideline personnel to evaluate the player(s) consistent with that explained above.

Figure 2:
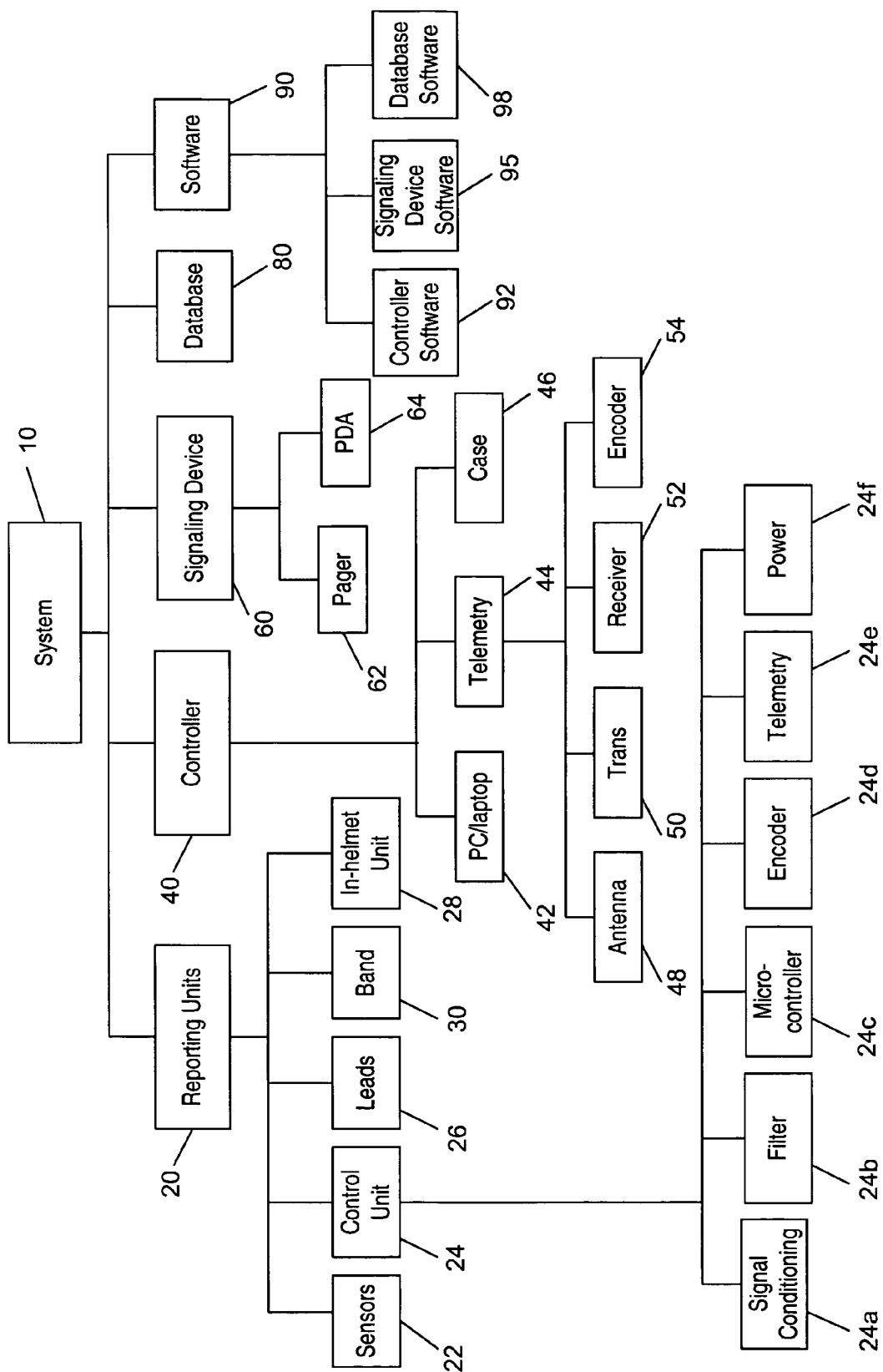
FIG. 2 is a schematic of the system of the invention.

Referring to FIGS. 1 and 2, the system 10 includes at least one database 80 configured to store and provide access to parameter data measured by the reporting devices 20 and calculated data from the controller 40 and the signaling device 60. For example, the database 80 serves as a team administrator database for the athletic department of a college or university, wherein the database 80 functions as an interactive clearinghouse or warehouse for all athlete information shared among various departments or sports. The database 80 is internet enabled to provide remote access to authorized users, including coaches, trainers, equipment managers and administrators, which allows the users to keep abreast of changes in players' status. The database 80 also provides a host of administrative and management tools for the team and administrative staff. The database 80 can be a component of the college's broader computer network system and interact with other databases associated with the system 10. On a smaller level, such as that found in high schools, the database 80 can be located on the sideline controller 40, wherein personnel associated with the high school have access, either direct or remote.

As briefly explained above, the system 10 is integrated with a method 100 for evaluating and treating a player. The method 100 includes a number of steps to be performed by qualified sideline personnel, such as trainers, coaches, and/or medical staff, which typically are on or near the sidelines of a sporting event or practice. The method 100 can be initiated in multiple ways: first, when the system 10 detects an Alert Event; second, when qualified sideline personnel observe an elevated physiological parameter or signs thereof, such as an impact to a player or signs that the player sustained an impact; and third, when a player self-reports elevated physiological parameters, such as an impact or the effects of an impact. Regarding the first way to initiate the method 100 and consistent with that explained above, the Alert Event is conveyed to the sideline personnel via the controller 40 and/or the signaling device 60. One of skill in the art recognizes that the last two ways to initiate the method 100 are subjective and can be based upon the sideline personnel's experience and level of training, as well as the player's level of experience and cooperation.

In one embodiment, the method 100 utilizes a software package or interactive wizards 95 that are loaded onto the signaling device 60, such as the PDA 64. As discussed above, when an Alert Event is detected, the controller 40 sends a signal to the signaling device 60 providing relevant information about the Alert Event. For each Alert Event, the signaling device 60 displays the affected player's number and medical history, the time of the event, and the physiological parameter to be evaluated. In the situation where a head impact results in an Alert Event, the signaling device 60 displays the point of impact on the player's head, the cumulative impacts sustained by the player during the current sporting session, and graphs the magnitude and duration of recent impacts to the player.

The interactive wizards 95 provide testing baselines and an interactive protocol for guiding sideline personnel through appropriate examination procedures. The signaling device 60 records the results and transmits the results to the controller 40 and/or the database 80 for use in further evaluation and treatment of the player. Therefore, whenever an Alert Event occurs and a potentially injured player is brought to the sideline for evaluation, the signaling device 60 displays the individual's medical and injury history, the results of previous evaluations and other pertinent medical data. Then, the signaling device 60, through the interactive wizards 95, prompts the sideline personnel to conduct the appropriate sideline examination, records the responses, compares the results to established baselines, and may prompt further testing. The sideline personnel, which may include certified trainers and/or medical staff, such as physicians, utilize the stored results to evaluate the severity of the player's condition and to make a return to play (RTP) decision or a no return to play decision for the player. In that latter situation, the player is prevented from playing for a period of time while further observation and testing may be conducted. Additionally, the signaling device 60 can be programmed with wizard programs 95 that assure best practices are followed in the treatment and documentation of mild traumatic brain injuries (MTBI) and elevated body temperatures.

In another embodiment where the reporting units 20 and the controller 40 are omitted from the system 10, the signaling device 60 is utilized to evaluate and treat the player after the player self-reports an elevated physiological parameters, or qualified sideline personnel observe an elevated physiological parameters. In this manner, the number of components within the system 10 is reduced; however, the method 100 of evaluating and treating a player remains constant through the use of the signaling device 60 and its interactive wizards. Therefore, the device 60 utilizes the interactive wizard programs 95 to provide testing baselines and an interactive protocol for guiding sideline personnel through the appropriate examination procedures.

The wireless signaling device 60 is designed to operate as an interactive sideline assistant, providing and receiving necessary equipment and medical information for the evaluation and treatment of players. Thus, the signaling device 60 features wizards, which are integrated, interactive software programs 95 that provide injury/physiological parameter assessment and team management tools. In one embodiment, the wizard software package 95 includes a roster program which contains all the basic information about each individual player: e.g., contact information, which sports they play (including position and jersey number), emergency information, relevant sizes, equipment issues and availability to play. Information can be stored and sorted in a variety of ways, such as by team, person, item and size. The software program 95 includes linked features, such that sideline personnel can access the player's medical history and risk factors by selecting the player's name, identifier or uniform number. After an Alert Event has occurred and to assist the sideline personnel with conducting the evaluation and treatment method 100, the wizard software 95 provides on-field steps, off-field steps and return-to-play sequences. As part of the method 100, the sideline personnel are prompted by the wizard software 95 to perform the steps and sequences to evaluate and treat the player(s) in question. The signaling device 60 software also includes a session manager program that allows the coaching staff to document incidents as they occur during a practice or a game. The appropriate information about the team, players and conditions (e.g., weather and field conditions, such as artificial turf or natural grass) is entered at the beginning of each session. Then, as injuries or suspected injuries occur, the wizard programs 95 provide a template for recording injury data by player.

The system 10 includes both on-field aspects and off-field communication aspects that enable the components of the system 10 to communicate and perform the method 100. Regarding the on-field communication aspects, the reporting units 20, the sideline controller 40, the signaling device(s) 60 and the database 80 communicate to provide event data, historical data, and impact data whereby the sideline personnel can evaluate and treat a player that sustains an Alert Event. Regarding the off-field communication aspects, the medical staff, the coaching staff, and/or the training staff can access data and information hosted by the database 80 to manage the diagnosis and/or treatment of various players. For example, the medical staff can log onto a management software program 98 hosted by the database 80 to review a player's medical history and course of treatment as part of the follow-up evaluation and the RTP decision. The internet-based software program 98 used for off-field aspects is secure such that only authorized users can access player data, medical histories, and treatment information.

FIGS. 5-10 provide a flowchart of the method 100 of evaluating and treating a player that sustains an Alert Event based upon an impact to the head resulting in a possible concussion. The method 100 commences in one of three ways: first, when the system 10 detects an Alert Event and conveys it to the sideline personnel, via the sideline controller 40 or the signaling device 60; second, when the sideline personnel observe a significant impact to a player or signs that the player sustained a significant impact; and third, when a player self-reports an impact or the effects of an impact.

The first step or component of the method 100 involves an on-field inquiry 200 by the sideline personnel to ascertain the severity of the impact. As part of the on-field inquiry 200, the sideline personnel should determine whether the player has suffered a loss of consciousness (LOC) and the time duration of the LOC. Provided the player has not suffered a neck injury, experiences bleeding, or displays other serious symptoms, the sideline personnel utilizes the signaling device 60 to presumably grade the concussion as mild, moderate or severe. Due to the fact that the preliminary grading of the concussion into one of three categories is difficult, the concussion grading is subject to revision based upon further observation and the player recovery. Once the suspected concussion is preliminarily assessed or graded into one of these three categories, distinct treatment and evaluation protocols or sequences are provided by the method 100 for the sideline personnel to follow. Therefore, once the level of the concussion is determined, the method 100 provides an interactive protocol for evaluation and treatment of the player that utilizes many evaluation tools, including the mini-battery, the player history, the player risk factors, and the sideline battery. The steps within the protocol enable the sideline personnel to determine whether the player should, among other things, be cleared for a return to play (RTP), further evaluated, or held out of additional play.

Figure 6A:
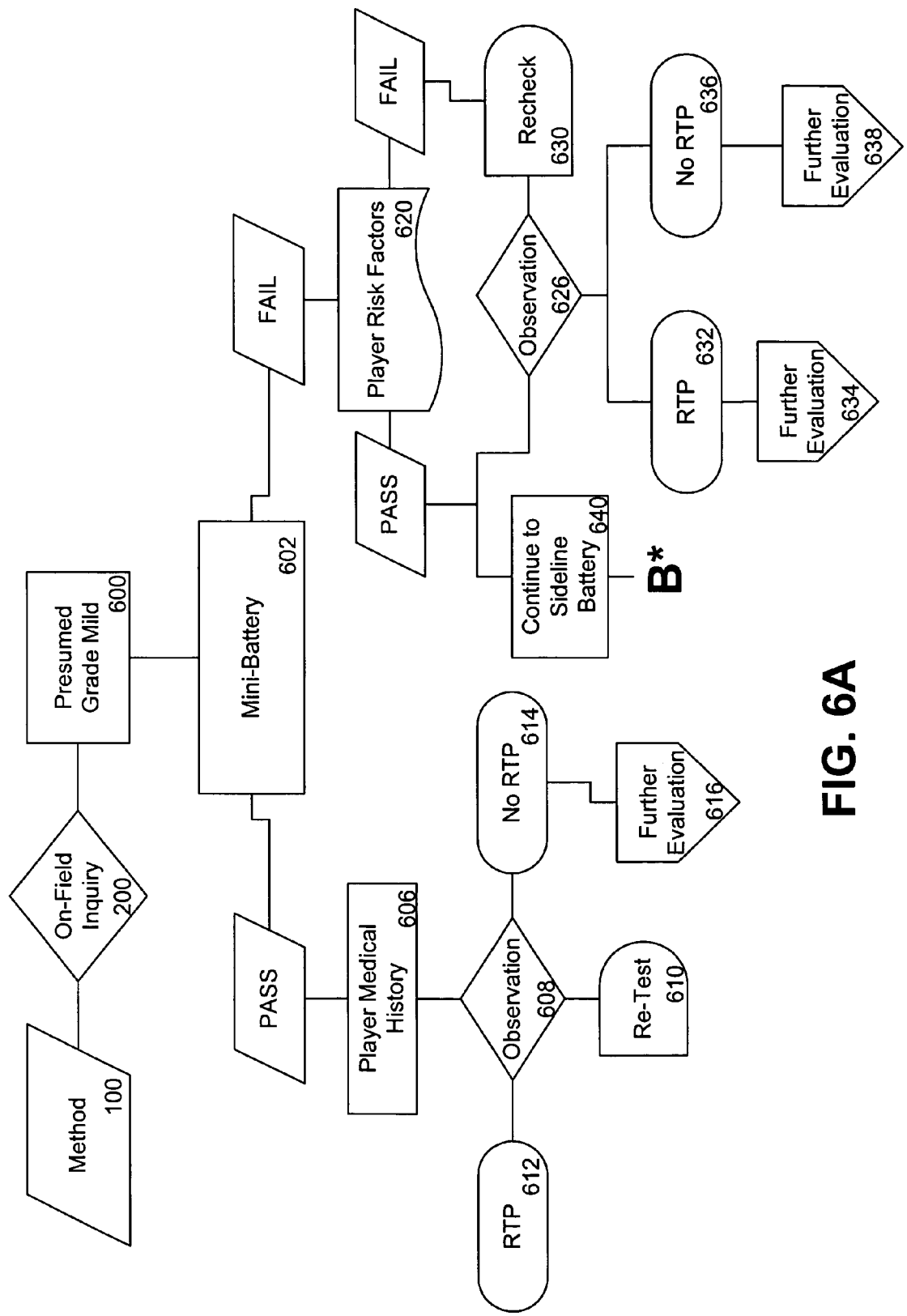
FIG. 6A is a flowchart of the method, showing a first portion of the evaluation and treatment sequence for a mild grade concussion.

Referring to FIG. 6A and assuming the on-field inquiry 200 results in the presumption of a mild grade concussion, the signaling device 60 prompts the sideline personnel to administer a mini-battery of questions 602. A mild grade concussion may be presumed if the player does not lose consciousness (LOC=0). The mini-battery 602 includes questions directed to the player's physical condition, (headache, nausea, vision), mental status (memory) and/or coordination. The response to each battery question is recorded by the signaling device 60, and the battery result is calculated by the device 60. If the player passes the mini-battery assessment 602, the sideline personnel consult the player's medical history 606 and conduct further observation 608. If the medical history 606 and the subsequent observation 608 provide positive results, the sideline personnel can clear the player for a return to play 612. The observation 608, often conducted on the field or sidelines, involves an assessment of whether the player has a speech disturbance, signs of trauma, respiratory troubles, recollection of the impact or hit, coordination or balance problems, and evaluation of the player's eyes for size, light sensitivity and movement. If the medical history 606 and the subsequent observation 608 provide negative results, the device 60 issues a no return to play (No RTP) warning 614 and further evaluation 616 is scheduled by the signaling device 60 for at least the next 48 hours. If the medical history 606 and the subsequent observation 608 are inconclusive, the sideline personnel can re-perform 610 the mini-battery 602 as step 610 and proceed as explained.

If the player fails the mini-battery 602, the player's medical history and/or risk factor information, including injury and treatment histories, are displayed on the signaling device 60. In most instances, the sideline personnel determine whether the player has passed or failed the mini-battery 602. However, depending upon the sophistication of the wizard program 95, the device 60 can require confirmation of the conclusion reached by the sideline personnel, or in some cases, bypass the conclusion reached by the sideline personnel, wherein the training and experience of the sideline personnel is taken into account by the wizard program 95. Similarly, the player's risk factors can also be displayed on the signaling device 60 as part of the mini-battery 602. If the review of the medical history and risk factors 620 is negative, the player is restricted from further play until further observation 626 and a re-check 630 are conducted. In the event the observation 626 and the re-check 630 are positive, the player can be returned to play 632 and the signaling device 60 schedules further evaluation 634 over at least the next 48 hours. In the event the observation 626 is negative, the device 60 issues a no return to play warning 636, and the signaling device 60 again schedules further evaluation 638 over at least the next 48 hours.

Figure 6B:
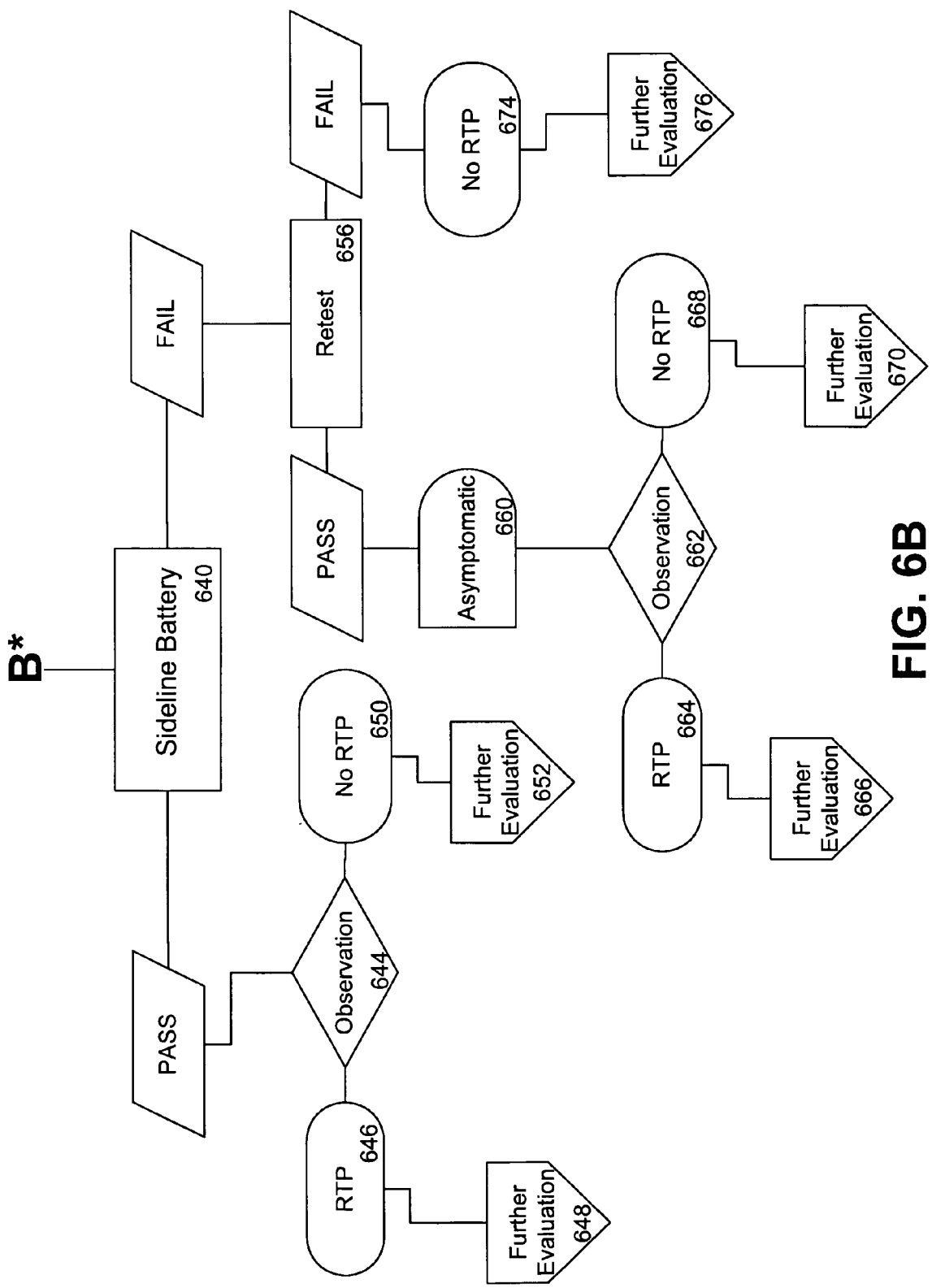
FIG. 6B is a flowchart of the method, showing a second portion of the evaluation and treatment sequence for a mild grade concussion.

If the review of the medical history and risk factors 620 provides a satisfactory observation 626 result, a more comprehensive sideline battery of tests 640 is performed on the player (see FIG. 6B). The sideline battery 640 involves a number of steps, including the comprehensive observation of the player's physical condition and application of standardized concussion criteria, such as the Standardized Assessment of Concussion (SAC) questions. The signaling device 60 prompts the sideline personnel throughout the battery 640 and displays and records the result of the battery 640. In the event the sideline personnel logged into the signaling device 60 is not qualified to run the battery 640, due to a lack of training or experience, the device 640 provides an alert advising of such. If the battery 640 results are positive, an observation 644 similar to observation 608 is conducted. If the observation 644 proves satisfactory, the sideline personnel can clear the player for a return to play 646 with further evaluation 648 to be scheduled by the signaling device 60. If the observation 644 provides negative results, the device 60 provides a warning recommending that the player not be permitted to return to play (No RTP) 650 and further evaluation 652 is scheduled by the signaling device 60 for at least the next 48 hours. In the event the sideline personnel ignore the no return to play warnings provided by the device 60, the device 60 may request and record confirmation of the sideline personnel's decision. The device 60 can detect the sideline personnel's decision to ignore the warning by monitoring whether the sideline personnel attempts to return a player to the active roster list on the wizard program 95.

If the battery 640 results are negative, then the player is retested with the sideline battery 640 as step 656. In the event the player fails the battery retest 656, the device 60 provides a recommendation that the player not be permitted to return to play 674 and further evaluation 676 is scheduled by the signaling device 60 for at least the next 48 hours. In the event the player passes the battery retest 656, the sideline personnel are instructed by the signaling device 60 to monitor the player and verify that the player is asymptomatic or not exhibiting concussion symptoms 660 for a period of time after the impact, such as twenty minutes. The asymptomatic time period varies with a number of factors, including but not limited to the nature of the physiological parameter to be measured by the system 10, the age and experience of the player, the medical history of the player, the presence or absence of risk factors, and the type and intensity of the sporting activity, and the ambient conditions (e.g., temperature, humidity and heat index). The sideline personnel continue to observe 662 the player, wherein the player can return to play 664 if the observation 662 is positive and further evaluation 666 is scheduled by the signaling device 60. The device 60 warns the sideline personnel that the player should not be permitted to return to play 668 if the observation 662 is negative and the signaling device 60 schedules further evaluations 670.

As shown in FIGS. 6A and 6B, the signaling device 60 utilizes the wizard software 95 to guide the sideline personnel through the steps of the method 10 to evaluate and treat a mild concussion with the use of prompts and instructions. The device 60 stores the data and results of the tests administered by the sideline personnel for subsequent review and evaluation, including that conducted by medical personnel. Also, the device can transfer or upload the test data and results to the controller 40 and/or database 80 for subsequent review and evaluation. In this manner, the test data and results are integrated into the player's medical history such that the data and results are available to the sideline personnel when the method 10 is subsequently performed, for example in a later game during the season or the next year. Accordingly, the system 10 and the method 100 provide an interactive platform for impact monitoring, evaluation and treatment, wherein earlier test results and data are accessible for the evaluation and treatment of a current condition.

Figure 7:
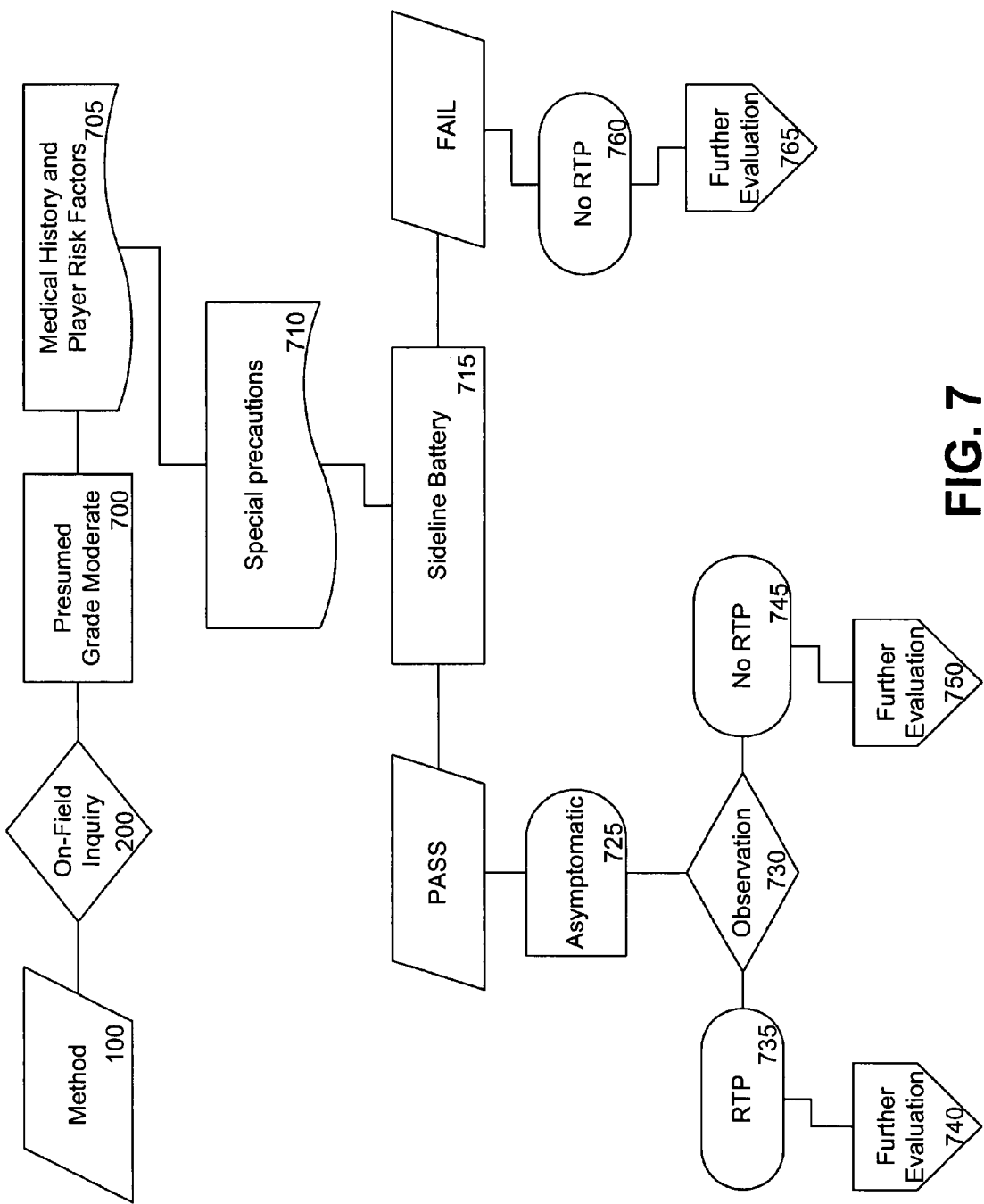
FIG. 7 is a flowchart of the method, showing the evaluation and treatment sequence for a moderate grade concussion.

Referring to FIG. 7 and assuming the on-field inquiry 200 results in the presumption of a moderate grade concussion, the signaling device 60 provides the player's medical history and risk factors 705 for consideration by the sideline personnel. A moderate grade concussion may be presumed if the player loses consciousness for less than one minute (LOC<1 minute). After the history and risk factors 705 are considered, the device 60 graphically provides a list of special precautions 710 for the sideline personnel to consider in light of the moderate grade concussion. These precautions 710 are consistent with the standardized warnings for the physiological parameter measured, such as the SAC standards, and may include instructions to observe the physical and/or mental status of the player for an interval of time. Next, the device 60 prompts the sideline personnel to conduct the sideline battery 715, as explained above (see battery 640 above). If the player fails the battery 715, the player is not permitted to return to play 760 and further evaluation 765 is scheduled by the signaling device 60 for at least the next 48 hours. If the player passes the battery 715, the sideline personnel are instructed by the signaling device 60 to monitor the player and verify that the player is asymptomatic or not exhibiting concussion symptoms 725 for a period of time after the impact, such as twenty minutes. The sideline personnel continue to observe 730 the player, wherein the player can return to play 735 if the observation 730 is positive and further evaluation 740 is scheduled by the signaling device 60 for at least the next 48 hours. The device 60 issues a warning recommending that the player should not be permitted to return to play 745 if the observation 730 is negative and the signaling device 60 schedules further evaluations 750.

Figure 8:
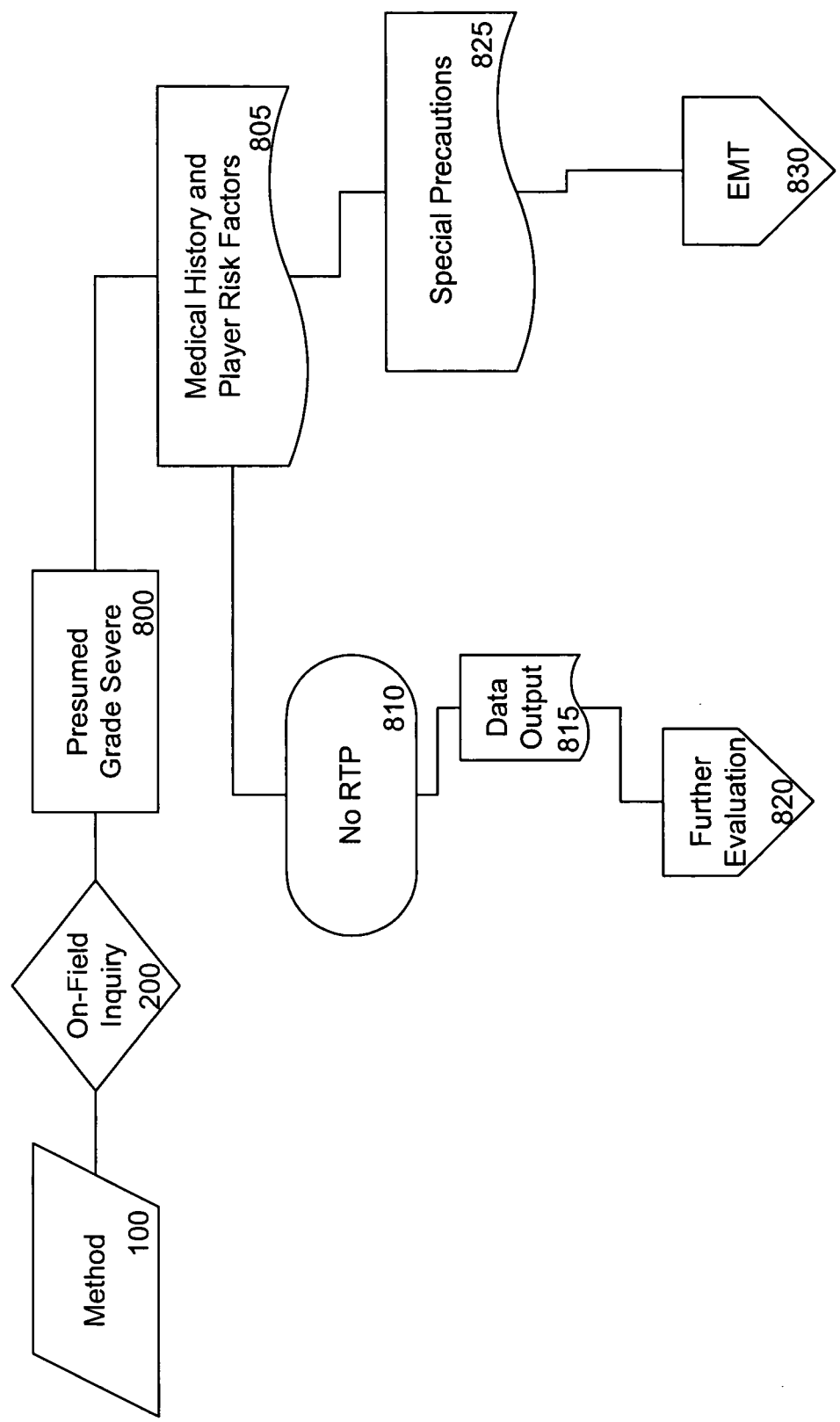
FIG. 8 is a flowchart of the method, showing the evaluation and treatment sequence for a severe grade concussion.
Figure 9:
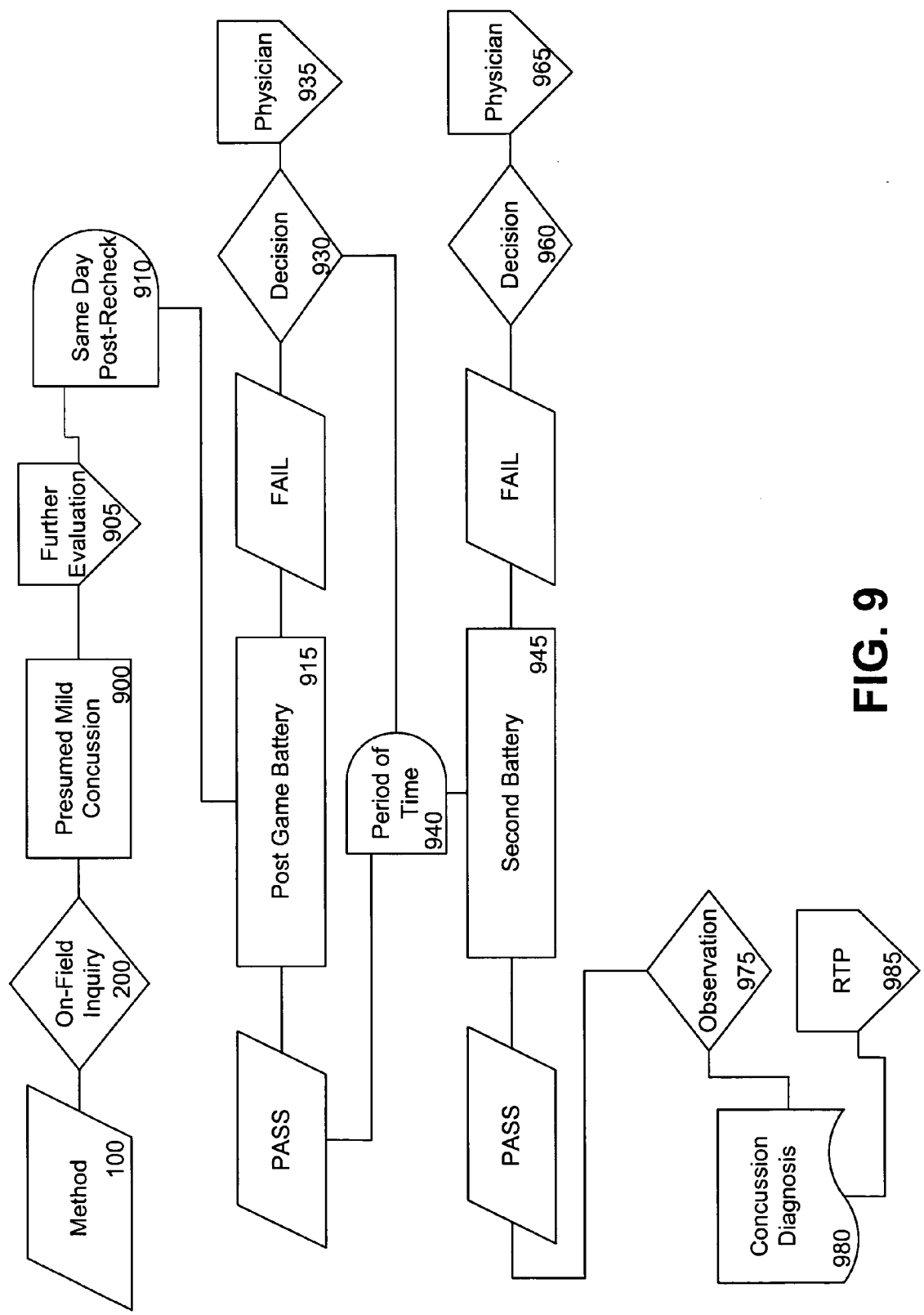
FIG. 9 is a flowchart of the method, showing the evaluation and treatment sequence for off-field evaluation and a mild grade concussion; and, FIG. 10 is a flowchart of the method, showing the evaluation and treatment sequence for a return to play (RTP) decision where the player has sustained his first mild or moderate concussion of the season.

Referring to FIG. 8 and assuming the on-field inquiry 200 results in the presumption of a severe grade concussion, the signaling device 60 provides the player's medical history and risk factors 805 for consideration by the sideline personnel. A severe grade concussion may be presumed if the player loses consciousness for greater than or equal to one minute (LOC>1 minute). After the player's history and risk factors 805 are considered, the device 60 graphically provides a list of special precautions 825 for the sideline personnel to consider in light of the moderate grade concussion. These precautions are consistent with the standardized warnings for the physiological parameter measured, such as the SAC standards, and may include instructions to observe the physical and/or mental status of the player for an interval of time. Depending upon the player's risk factors 805 and the consideration of the special precautions 825, the device 60 advises with a warning that the player should not be not permitted to return to play 810 and further evaluation 820 is scheduled by the signaling device 60. In addition, the device 60 can provide a data output 815 that reports on the player's condition via the sideline unit 40 or a remote printer. Alternatively, if the player's vital signs do not stabilize and/or the player experiences difficulty remaining conscious, the device 60 instructs the sideline personnel to seek immediate emergency medical treatment (EMT) 830 for the player.

As mentioned above, the method 100 has both on-field and off-field communication aspects. Whereas FIGS. 5-8 primarily concerned on-field communication aspects, FIG. 9 outlines the off-field communication protocol for a mild concussion. Once the mild grade concussion 900 is presumed, further evaluation 905 and a same day, post-event recheck are performed 910. Next, a post game test battery 915 is performed, wherein the battery 915 involves assessing the player's condition with the standardized tests, such as the post-concussion symptoms score (PCSS) and the presence of post traumatic amnesia (PTA). If the player fails the battery 915, further decision and/or observation 930 is required by the device 60 with elevation to a physician 935 if the player's condition does not improve. If the player passes the battery 915, the device 60 instructs the sideline personnel to perform a second battery 945 again after a period of time 940, such as twenty-four hours. If the player fails the second battery 945, the device 60 requires further decision and/or observation 960 and elevation to physician 965, as explained above. The further decision and/or observation 930, 960 steps may include a statistical evaluation of the results and any changes therein, such as reliable change index (RCI), to determine if the player should see a physician or specialist. The concussion management team can utilize the RCI for additional guidance since it provides a criterion value above which an observed change in the player's condition and/or battery results can be considered meaningful. If the player passes the second battery 945, further observation 975 is conducted with a formal diagnosis 980 to be rendered. Following the diagnosis 980, which can involve a printed report, the player can be cleared for a return to play 985 after the treatment steps are completed. Alternatively, additional test batteries may be performed after the observation 960 and an additional period of time.

Accordingly, the system 10 and the method 100 include both on-field and off-field aspects which are integrated and displayed on the signaling device 60, wherein the device 60 prompts the sideline personnel to perform tasks and records results for review and analysis in order to treat the player.

Figure 10:
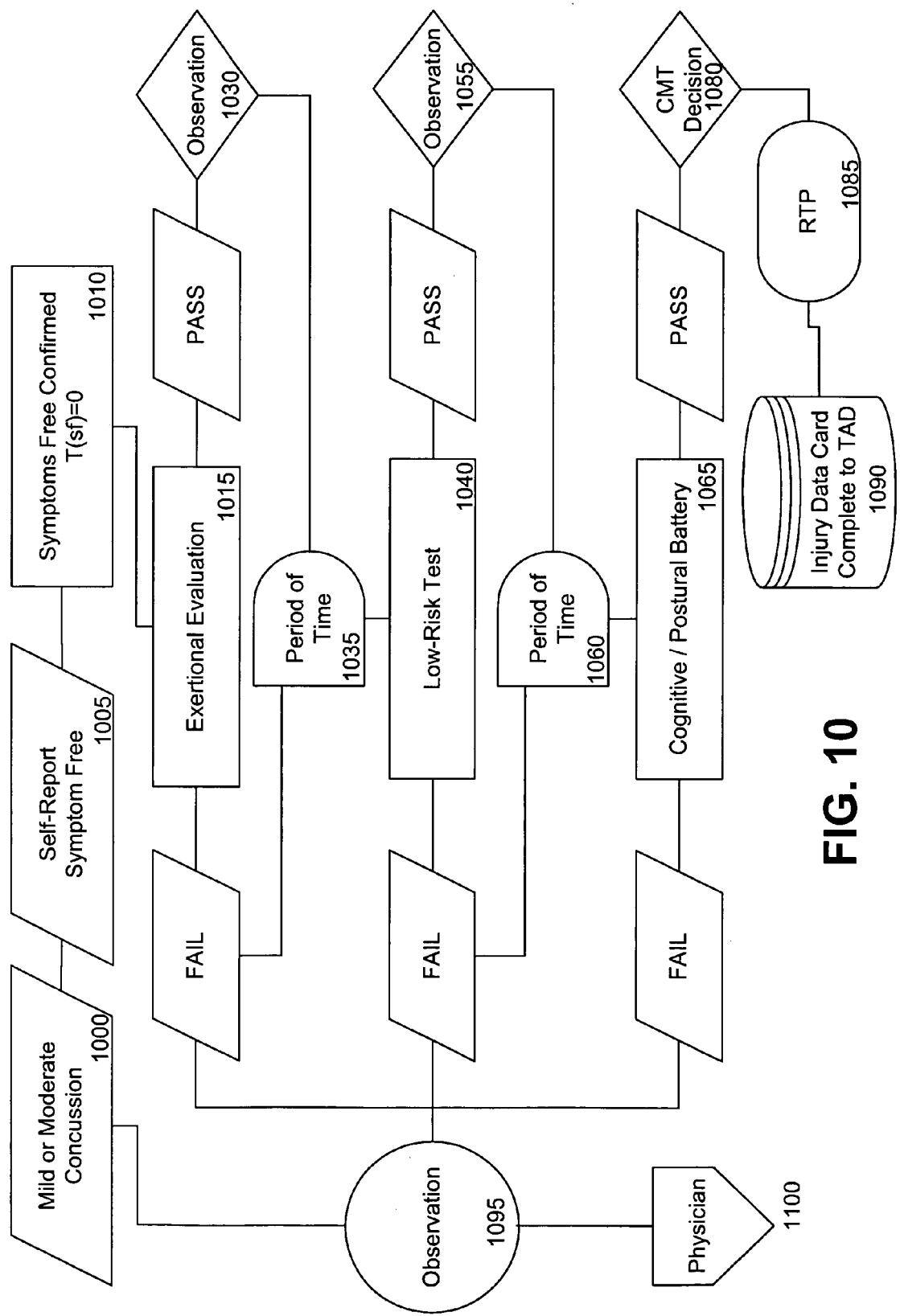

A return to play (RTP) protocol of the method 100 for a mild or moderate grade concussion is shown in FIG. 10. Typically, the RTP decision for a player is made after discussions among a number of parties, including the training staff, the team and personal physicians, any referral sources. These parties may define the concussion management team (CMT). In most situations, returning an athlete to participation should follow a progression that begins once the athlete is completely symptom free. Preferably, evaluations are performed when the player is at rest and after exertional maneuvers such as biking, jogging, sit-ups and push-ups. Baseline measurements of neuropsychological (NP) testing and postural stability can be used for comparison purposes.

An example of the RTP protocol for a player who experiences a mild or moderate concussion is shown in FIG. 10. If the player reports no symptoms of the concussion 1005 and such is confirmed with testing 1010, an exertional evaluation 1015 is conducted. If the player fails the evaluation 1015, further observation 1095 is conducted and a physician may be consulted 1100. Alternatively and after a first period of time since the no symptom self-report 1005, a sport specific low-risk test 1040 is conducted. If the player passes the evaluation 1015, further observation 1095 is conducted and after a period of time 1035 since the no symptom self report 1005, the sport specific low-risk test 1040 is performed. The test 1040 is sport dependent, and may include lining up in a three-point stance or catching and throwing a football. If the player fails the low-risk test 1040, further observation 1095 is again conducted and a physician may be consulted 1100. Alternatively, and after a second period of time since the no symptom self report 1005, the player may undergo a cognitive/postural test battery 1065. If the player passes the low-risk test 1040, further observation 1055 is conducted and after the second period of time 1060, a cognitive/postural battery 1065 is performed. If the player fails the battery 1065, further observation 1095 is again conducted and a physician may be consulted 1100. If the player passes the battery 1065, the concussion management team (CMT) consults and may agree to allow the player to return to play 1085 in the next practice or game. Once the player has been cleared for a return to play 1085, the "data card," a file containing the relevant injury data and information, is returned to the database 80 whereupon it becomes available for subsequent use by the sideline personnel. In this manner, a player's medical history is current when accessed by the sideline personnel on the signaling device 60 to evaluate and treat a subsequent condition.

To conduct the interactive protocol of the method 100, the signaling device 60 includes software wizards 95 that allows for the display of: a team roster; the player history, including on-field incident recordings; the mini-battery 602; the sideline battery 640; and, the summary of each battery with color-coded pass/fail results. The controller 40 also includes software 92 that provides a variety of displays for consideration on the sideline or away from the playing field. For example, the displays on the wireless PDA 60 and the display 42 of the controller 40 can show a pictorial representation of a single impact and cumulative impacts to the player's head region. The display can also indicate a number of conditions, including which players by number are in communication with the system 10. As another example, the system 10 can be configured to graphically display the cumulative impacts on a grid showing magnitude, duration, and location. The level and complexity of the displayed information can be customized based upon a number of factors, including the training and experience of the sideline personnel, and the precise components and features of the system 10.

While the foregoing examples relate to an impact to the player's head, it is understood that the system 10 and method 100 can be applied to evaluate and treat the effects of an impact to a different body part. For example, components of the system 10 can be integrated into a shoulder pad assembly or knee pad assembly, wherein the method 100 is applicable to evaluate and treat an impact to the torso region or the knee. Essentially, the system 10 and the method 100 can be configured for use with body parts other than the head and protective equipment other than a helmet. In addition, the system 10 and method 100 can be configured to monitor other physiological parameters. For example, the system 10 can monitor the player's body temperature and the method 100 can provide evaluation and treatment protocols when the player's body temperature exceeds a predefined threshold.

While the specific embodiments have been illustrated and described, numerous modifications come to mind without significantly departing from the spirit of the invention, and the scope of protection is only limited by the scope of the accompanying Claims.

What is claimed is:

1. A method for monitoring a specific player from among a larger group of players engaged in a sporting activity based upon monitoring of physiological parameters of the specific player, the method comprising steps of:
   providing a system having a plurality of reporting units and a signaling device, each reporting unit being associated with a specific player and having an encoder and a sensor, the encoder provides a unique identifier for the specific player;
   utilizing the sensor to monitor the physiological parameter of the specific player and to generate parameter data while that specific player is engaged in the sporting activity;
   calculating a parameter result based upon sensor data encoded with the unique identifier, and comparing said result to a predetermined threshold; and
   sending an alert to the signaling device when the parameter result exceeds the threshold for said specific player.

2. The method of claim 1, further comprising steps of:
   providing an evaluation protocol on the signaling device for said specific player; and
   evaluating said specific player according to the evaluation protocol.

3. The method of claim 2, further comprising a step of providing a treatment protocol on the signaling device for said specific player based upon the results of the evaluation protocol.

4. The method of claim 3, wherein the step of providing a treatment protocol utilizes an interactive software program on the signaling device that prompts a user to perform certain tasks and records the completion of the tasks.

5. The method of claim 2, wherein the step of providing an evaluation protocol utilizes an interactive software program on the signaling device that prompts a user to perform certain tests and records test results.

6. The method of claim 1, wherein the step of calculating the parameter result and comparing said results to said predetermined threshold occurs in the reporting units.

7. The method of claim 1, wherein the system further includes a controller unit that receives data regarding the physiological parameter from the reporting units and then calculates the parameter result.

8. The method of claim 7, wherein the reporting units have a transmitter and the controller has a receiver for wireless transmission of physiological parameter data.

9. The method of claim 1, wherein the step of sending the alert to the signaling device includes sending the alert via wireless transmission.

10. The method of claim 1, wherein the signaling device includes a pager or a personal digital assistant.

11. A method for monitoring, evaluating and treating a sports player on a team of players engaged in a sporting activity, the method comprising steps of:
providing a system having a plurality of reporting units, a controller unit, and a signaling device, each reporting unit being associated with a specific player and having an encoder that provides a unique identifier for the specific player, the reporting unit also having an array of sensors to monitor physiological parameters of the player while said player is engaged in the sporting activity;
transmitting data encoded with the unique identifier regarding the physiological parameters from the reporting units to the controller unit;
calculating a parameter result from the encoded data with the controller unit and comparing said result to a predetermined threshold; and
sending an alert from the controller unit to the signaling device when the parameter result exceeds the threshold for a specific player.

12. The method of claim 11, further comprising steps of:
providing an evaluation protocol on the signaling device for the specific player relating to the parameter result that exceeds the threshold; and,
evaluating said specific player according to the evaluation protocol.

13. The method of claim 12, further comprising a step of providing a treatment protocol on the signaling device relating to the parameter result that exceeds the threshold.

14. The method of claim 13, wherein the treatment protocol provides a warning that the player is restricted from further play.

15. The method of claim 11, wherein the reporting units wirelessly transmit physiological parameter data to the controller unit.

16. The method of claim 11, wherein a wired connection is used to transmit physiological parameter data from the reporting units to the controller unit.

17. The method of claim 11, wherein the physiological parameter monitored by the sensor array is acceleration of the player's head.

18. The method of claim 11, wherein the physiological parameter monitored by the sensor array is the temperature of the player.

19. The method of claim 11, wherein the signaling device includes a pager or a personal digital assistant.

20. A portable electronic device for evaluating and treating a player engaged in sporting activity, the portable electronic device comprising:
an evaluation protocol for the evaluation of a physiological parameter of the player engaged in the sporting activity, the evaluation protocol having interactive prompts to require a user who is not the player to input data; and,
a treatment protocol for the treatment of the player based upon said physiological parameter, the treatment protocol having interactive prompts for the user and being capable of issuing warnings to said user based upon player data inputted by the user.

21. The portable electronic device of claim 20, wherein the device is a personal digital assistant.

22. The portable electronic device of claim 21, wherein the personal digital assistant graphically displays the evaluation protocol.

23. The portable electronic device of claim 21, wherein the personal digital assistant graphically displays the treatment protocol.

24. A system for monitoring physiological parameters of players engaged in a sports activity, the system comprising:
a plurality of reporting units, each reporting unit being associated with an individual player and having at least one sensor that measures a physiological parameter data of said player while said player is engaged in the sporting activity, each reporting unit further having an encoder that encodes said physiological parameter data with a unique identifier corresponding to said player;
a controller that receives said physiological parameter data encoded with the unique identifier corresponding to a player and transmitted from each reporting unit, wherein the controller multiplexes encoded physiological parameter data transmitted from the reporting units and calculates a parameter result that defines an alert event when said parameter result surpasses a predetermined value; and
a signaling device that provides an alert upon the occurrence of the alert event.

25. The system of claim 24, wherein the signaling device has one of either an interactive treatment protocol for a user who is not the player to treat said player or an interactive evaluation protocol for a user who is not the player to evaluate the player that experienced the alert event.

26. The system of claim 24, wherein the signaling device includes a user interface that displays at least one of: an identification of the player, a time associated with the parameter result, and the location on the player's body associated with the parameter result.

27. The system of claim 24, wherein the signaling device includes a pager or a personal digital assistant.

28. The system of claim 24, wherein:
each reporting unit includes a microprocessor, a telemetry element, and a battery power supply, wherein the reporting unit resides entirely within a helmet of an individual player, and
the telemetry unit transmits physiological parameter data measured by the sensor to the controller.

29. The system of claim 24, wherein the physiological parameter measured by the system is the acceleration of a player's body part that experiences an impact.

30. The system of claim 24, wherein the physiological parameter measured by the system is the player's body temperature.

31. A system for monitoring a physiological parameter of players engaged in a sports activity, the system comprising:
a plurality of reporting units, wherein a reporting unit resides entirely within a helmet of an individual player and includes at least one sensor that measures a physiological parameter data of said player, the reporting unit further includes an encoder that encodes the physiological parameter data measured by the sensor with a unique player identifier, wherein both the measuring step and the encoding step occur while the players are engaged in the sports activity; and,
a signaling device that wirelessly receives and multiplexes the encoded physiological parameter data from each of the reporting units, the signaling device providing an alert for a specific player when a parameter result for the specific player surpasses a predetermined value.

32. The monitoring system of claim 31, wherein the sensor is a thermistor configured to measure the player's temperature.

33. The monitoring system of claim 31, wherein the signaling device provides an evaluation protocol that prompts a user to perform certain tasks to evaluate the specific player when the parameter result surpasses the predetermined value.

34. The monitoring system of claim 31, wherein the signaling device includes a user interface that displays at least one of: an identification of the specific player, a time associated with the parameter result, and the player's medical history.

35. The monitoring system of claim 31, wherein:
each reporting unit includes a microprocessor, a telemetry element, and a battery power supply, wherein the reporting unit resides entirely within a helmet of an individual player, and
the telemetry unit transmits physiological parameter data measured by the sensor to the signaling device.

36. A system for monitoring a physiological parameter of players engaged in a sports activity, the system comprising:
a plurality of reporting units, wherein a reporting unit resides entirely within a helmet of an individual player and includes at least one sensor that measures a physiological parameter of said player, the reporting unit further includes an encoder that encodes the physiological parameter data of said player with a unique player identifier, wherein both the measuring step and the encoding step occur while the players are engaged in the sports activity; and,
a controller that wirelessly receives and multiplexes said encoded physiological parameter data, wherein the controller utilizes said encoded physiological parameter data to calculate a parameter result that defines an alert event when said parameter result surpasses a predetermined value.

37. The system of claim 36, wherein the physiological parameter measured by the sensor is acceleration due an impact to the player's helmet.

38. The system of claim 36, wherein the physiological parameter measured by the sensor is the player's body temperature.

39. The system of claim 36, wherein the controller has an interactive evaluation protocol to evaluate the player that experienced the alert event.

40. The system of claim 36, wherein the controller has an interactive treatment protocol to treat the specific player that experienced the alert event.

41. The system of claim 36, wherein the controller includes a user interface that, for each alert event, displays the player's identification and the time of the alert event.

42. The system of claim 36, further comprising a remote signaling device that provides an alert upon the occurrence of the alert event.

43. The system of claim 42, wherein the signaling device has one of either an interactive treatment protocol to treat said player or an interactive evaluation protocol to evaluate the player that experienced the alert event.

44. The system of claim 42, wherein the signaling device includes a user interface that, for each alert event, displays the player's identification and the time of the alert event.

45. A method for monitoring a specific player from among a larger group of players engaged in a sporting activity based upon monitoring of physiological parameters of the specific player, the method comprising steps of:
providing a system having a plurality of reporting units and a signaling device, each reporting unit being associated with a specific player and having an encoder and a sensor, the encoder providing a unique identifier for the specific player;
utilizing the sensor to monitor a physiological parameter of the specific player while said player is engaged in the sporting activity;
calculating a parameter result based upon sensor data encoded with the unique identifier, and comparing said result to a predetermined threshold;
sending an alert to the signaling device when the parameter result exceeds the threshold for said specific player;
wherein the physiological parameter measured by the system is the player's body temperature.

46. A system for monitoring physiological parameters of players engaged in a sports activity, the system comprising:
a plurality of reporting units, each reporting unit being associated with an individual player and having at least one sensor that monitors a physiological parameter of said player to generate parameter data while said player is engaged in the sports activity;
a controller that receives said parameter data encoded with a unique identifier corresponding to a specific player and transmitted from each reporting unit, wherein the controller multiplexes encoded parameter data transmitted from the reporting units and calculates a parameter result that defines an alert event when said parameter result surpasses a predetermined value; and
a signaling device that provides an alert upon the occurrence of the alert event,
wherein the physiological parameter measured by the system is the player's body temperature.

47. A system for monitoring a physiological parameter of players engaged in a sports activity, the system comprising:
a plurality of reporting units, wherein a reporting unit resides within a helmet of an individual player and includes at least one sensor that monitors a physiological parameter of said player to generate parameter data, the reporting unit further includes an encoder that encodes the parameter data with a unique player identifier, wherein the monitoring step, the generating step and the encoding step all occur while the player is engaged in the sports activity; and
a signaling device that wirelessly receives and multiplexes the encoded parameter data from each of the reporting units, the signaling device providing an alert for a specific player when a parameter result for the specific player surpasses a predetermined value,
wherein the sensor is a thermistor configured to measure the player's temperature.

48. A system for monitoring a physiological parameter of players engaged in a sports activity, the system comprising:
a plurality of reporting units, wherein a reporting unit resides within a helmet of an individual player and includes at least one sensor that measures a physiological parameter data of said individual player, the reporting unit calculating a parameter result from said physiological parameter data and comparing the parameter result against a predetermined parameter threshold, the reporting unit further having an encoder that encodes the parameter result with a unique player identifier for transmission when the parameter result surpasses the predetermined parameter threshold, wherein the measuring step, the calculating step, the comparing step and the encoding step all occur while the player is engaged in the sports activity; and, a signaling device that receives the encoded parameter result and provides an alert identifying the specific player with the parameter result that surpassed the predetermined parameter threshold.

* * * * *